(12) United States Patent
Roe et al.

(10) Patent No.: US 9,220,644 B2
(45) Date of Patent: Dec. 29, 2015

(54) ABSORBENT ARTICLE WITH IMPROVED GARMENT-LIKE CHARACTER

(75) Inventors: Donald Carroll Roe, West Chester, OH (US); Mark James Kline, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 408 days.

(21) Appl. No.: 13/034,784

(22) Filed: Feb. 25, 2011

(65) Prior Publication Data
US 2011/0208140 A1 Aug. 25, 2011

(30) Foreign Application Priority Data

Feb. 25, 2010 (CA) ..................................... 2692891

(51) Int. Cl.
| | | |
|---|---|---|
| A61F 13/49 | (2006.01) | |
| A61F 13/53 | (2006.01) | |
| A61F 13/534 | (2006.01) | |
| A61F 13/535 | (2006.01) | |
| A61F 13/532 | (2006.01) | |
| A61F 13/56 | (2006.01) | |

(52) U.S. Cl.
CPC ....... *A61F 13/5323* (2013.01); *A61F 13/49014* (2013.01); *A61F 13/535* (2013.01); *A61F 13/5622* (2013.01); *A61F 2013/530554* (2013.01)

(58) Field of Classification Search
CPC ............ A61F 2013/15357; A61F 2013/15373; A61F 2013/15382; A61F 2013/586–2013/587; A61F 2013/5355; A61F 13/62; A61F 13/535

USPC ................. 604/365–377, 385.21–385.23, 604/386–391; D24/124–126
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,387,207 A | 6/1983 | Edwards | |
| 4,463,045 A | 7/1984 | Ahr et al. | |

(Continued)

FOREIGN PATENT DOCUMENTS

| | | |
|---|---|---|
| EP | 433 951 B1 | 8/1996 |
| EP | 734 234 B1 | 6/2000 |

(Continued)

OTHER PUBLICATIONS

U.S. Appl. No. 13/034,784, filed Mar. 25, 2011, Donald Carroll Roe et al.

(Continued)

*Primary Examiner* — Lynne Anderson
*Assistant Examiner* — Kathryn E Ditmer
(74) *Attorney, Agent, or Firm* — Andrew J. Mueller

(57) ABSTRACT

A disposable absorbent article may include a chassis, an absorbent core, a pair of elastically elongatable ears and a pair of fastening tabs. The elastically elongatable ears and the fastening tabs have a transverse axis. The ears are connected to the chassis such that the transverse axis of the fastening tabs is located in specific portions of the article. The absorbent core is free of cellulosic fibers.

16 Claims, 21 Drawing Sheets

(56) References Cited

U.S. PATENT DOCUMENTS

| | | |
|---|---|---|
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |
| 4,673,402 A | 6/1987 | Weisman et al. |
| 4,685,915 A * | 8/1987 | Hasse et al. .................. 604/378 |
| 4,695,278 A | 9/1987 | Lawson |
| 4,699,622 A | 10/1987 | Toussant et al. |
| 4,785,996 A | 11/1988 | Ziecker et al. |
| 4,808,178 A | 2/1989 | Aziz et al. |
| 4,834,735 A | 5/1989 | Alemany et al. |
| 4,842,666 A | 6/1989 | Werenicz |
| 4,846,815 A | 7/1989 | Scripps |
| 4,856,504 A | 8/1989 | Yamamoto et al. |
| 4,861,652 A | 8/1989 | Lippert et al. |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,916,005 A | 4/1990 | Lippert et al. |
| 4,940,464 A | 7/1990 | Van Gompel et al. |
| 4,946,527 A | 8/1990 | Battrell |
| 4,963,140 A | 10/1990 | Robertson et al. |
| 4,968,312 A | 11/1990 | Khan |
| 4,990,147 A | 2/1991 | Freeland |
| 5,006,394 A | 4/1991 | Baird |
| 5,019,073 A | 5/1991 | Roessler et al. |
| 5,037,416 A | 8/1991 | Allen et al. |
| 5,062,840 A | 11/1991 | Holt et al. |
| 5,092,861 A | 3/1992 | Nomura et al. |
| 5,102,597 A | 4/1992 | Roe et al. |
| 5,137,537 A | 8/1992 | Herron et al. |
| 5,138,555 A | 8/1992 | Albrecht |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,171,236 A | 12/1992 | Dreier et al. |
| 5,176,671 A | 1/1993 | Roessler |
| 5,221,274 A | 6/1993 | Buell et al. |
| 5,234,423 A | 8/1993 | Alemany et al. |
| 5,242,436 A | 9/1993 | Weil et al. |
| 5,246,433 A | 9/1993 | Hasse et al. |
| 5,260,345 A | 11/1993 | Desmarais et al. |
| 5,269,775 A | 12/1993 | Freeland et al. |
| 5,306,266 A | 4/1994 | Freeland |
| 5,312,387 A | 5/1994 | Rossini et al. |
| 5,342,338 A | 8/1994 | Roe |
| 5,368,584 A | 11/1994 | Clear et al. |
| 5,380,313 A | 1/1995 | Goulait et al. |
| 5,383,872 A | 1/1995 | Roessler et al. |
| 5,387,207 A | 2/1995 | Dyer et al. |
| 5,397,316 A | 3/1995 | Lavon et al. |
| 5,397,318 A | 3/1995 | Dreier |
| 5,399,219 A | 3/1995 | Roessler et al. |
| 5,407,439 A | 4/1995 | Goulait |
| 5,460,622 A | 10/1995 | Dragoo et al. |
| 5,496,298 A | 3/1996 | Kuepper et al. |
| 5,499,978 A | 3/1996 | Buell et al. |
| 5,507,736 A | 4/1996 | Clear et al. |
| 5,514,121 A | 5/1996 | Roe et al. |
| 5,518,801 A | 5/1996 | Chappell et al. |
| 5,527,302 A | 6/1996 | Endres et al. |
| 5,540,671 A | 7/1996 | Dreier |
| 5,540,673 A | 7/1996 | Thomas et al. |
| 5,542,942 A | 8/1996 | Kline et al. |
| 5,549,592 A | 8/1996 | Fries et al. |
| 5,554,142 A | 9/1996 | Dreier et al. |
| 5,554,145 A | 9/1996 | Roe et al. |
| 5,569,233 A | 10/1996 | Goulait |
| 5,569,234 A | 10/1996 | Buell et al. |
| 5,569,900 A | 10/1996 | Blohbaum |
| 5,571,096 A | 11/1996 | Dobrin et al. |
| 5,580,411 A | 12/1996 | Nease et al. |
| 5,591,152 A | 1/1997 | Buell et al. |
| 5,593,399 A | 1/1997 | Tanzer et al. |
| 5,607,760 A | 3/1997 | Roe |
| 5,609,518 A | 3/1997 | Lucchesi |
| 5,609,587 A | 3/1997 | Roe |
| 5,635,191 A | 6/1997 | Roe et al. |
| 5,635,588 A | 6/1997 | Eshuis et al. |
| H1674 H | 8/1997 | Ames et al. |
| 5,653,703 A | 8/1997 | Roe et al. |
| 5,669,900 A | 9/1997 | Bullwinkel et al. |
| 5,672,404 A | 9/1997 | Callahan, Jr. et al. |
| 5,683,533 A | 11/1997 | Keighley et al. |
| 5,685,873 A | 11/1997 | Bruemmer |
| 5,705,013 A | 1/1998 | Nease et al. |
| H1732 H | 6/1998 | Johnson |
| 5,759,317 A | 6/1998 | Justmann |
| 5,797,824 A | 8/1998 | Tracy |
| 5,865,823 A | 2/1999 | Curro |
| 5,897,545 A | 4/1999 | Kline et al. |
| 5,899,895 A | 5/1999 | Robles et al. |
| 5,900,101 A | 5/1999 | Justmann |
| 5,904,675 A | 5/1999 | Laux et al. |
| 5,906,008 A | 5/1999 | Heki et al. |
| 5,938,648 A | 8/1999 | Lavon et al. |
| 5,941,864 A | 8/1999 | Roe |
| 5,947,946 A | 9/1999 | Fisher et al. |
| 5,947,948 A | 9/1999 | Roe et al. |
| 5,957,908 A | 9/1999 | Kline et al. |
| 5,968,025 A | 10/1999 | Roe et al. |
| 5,977,430 A | 11/1999 | Roe et al. |
| 5,993,433 A | 11/1999 | St. Louis et al. |
| 5,997,520 A | 12/1999 | Ahr et al. |
| 5,997,521 A | 12/1999 | Robles et al. |
| 6,004,306 A | 12/1999 | Robles et al. |
| 6,010,490 A | 1/2000 | Freeland et al. |
| 6,013,063 A | 1/2000 | Roe et al. |
| 6,107,537 A | 8/2000 | Elder et al. |
| 6,117,121 A | 9/2000 | Faulks et al. |
| 6,120,487 A | 9/2000 | Ashton |
| 6,120,489 A | 9/2000 | Johnson et al. |
| 6,132,411 A | 10/2000 | Huber et al. |
| 6,142,985 A | 11/2000 | Feist |
| 6,156,424 A | 12/2000 | Taylor |
| 6,168,584 B1 | 1/2001 | Allen et al. |
| 6,225,236 B1 | 5/2001 | Nishimoto et al. |
| 6,235,137 B1 | 5/2001 | Van Eperen et al. |
| 6,248,097 B1 | 6/2001 | Beitz et al. |
| 6,353,149 B1 | 3/2002 | Stone |
| 6,432,098 B1 | 8/2002 | Kline et al. |
| 6,454,753 B1 | 9/2002 | Shimoe et al. |
| 6,623,469 B1 | 9/2003 | Thomas |
| 6,652,693 B2 | 11/2003 | Burriss et al. |
| 6,680,422 B2 | 1/2004 | Roe |
| 6,716,441 B1 | 4/2004 | Osborne et al. |
| 7,028,735 B2 | 4/2006 | Schneider et al. |
| 7,056,411 B2 | 6/2006 | Desai et al. |
| 7,097,710 B2 | 8/2006 | Schneider |
| 7,169,228 B2 | 1/2007 | Schneider |
| 7,195,729 B2 | 3/2007 | Jackson et al. |
| 7,198,622 B2 | 4/2007 | Dahlgren |
| 7,222,654 B2 | 5/2007 | Schneider et al. |
| 7,361,167 B2 | 4/2008 | Erickson et al. |
| D579,110 S * | 10/2008 | Zink et al. .................. D24/126 |
| 7,432,413 B2 | 10/2008 | Roe et al. |
| 7,626,073 B2 | 12/2009 | Catalan |
| 7,799,162 B2 | 9/2010 | Wood et al. |
| 7,870,652 B2 | 1/2011 | Kline et al. |
| 2001/0053905 A1 | 12/2001 | Shingu et al. |
| 2003/0009144 A1 * | 1/2003 | Tanzer et al. .................. 604/391 |
| 2003/0077430 A1 | 4/2003 | Grimm et al. |
| 2003/0088220 A1 | 5/2003 | Molander et al. |
| 2003/0100878 A1 | 5/2003 | Leak et al. |
| 2003/0100879 A1 | 5/2003 | Kline et al. |
| 2003/0109844 A1 | 6/2003 | Gibbs |
| 2003/0233082 A1 | 12/2003 | Kline et al. |
| 2004/0063369 A1 | 4/2004 | Ahn et al. |
| 2004/0116888 A1 | 6/2004 | Dorschner |

(56) References Cited

U.S. PATENT DOCUMENTS

| | | |
|---|---|---|
| 2004/0122413 A1 | 6/2004 | Roessler et al. |
| 2004/0181200 A1 | 9/2004 | Desai et al. |
| 2004/0193133 A1 | 9/2004 | Desai et al. |
| 2005/0002767 A1 | 1/2005 | Oosterhouse |
| 2005/0004547 A1 | 1/2005 | Lavash |
| 2005/0009173 A1 | 1/2005 | Amand |
| 2005/0015938 A1 | 1/2005 | Shepard et al. |
| 2005/0027267 A1 | 2/2005 | Van Dyke et al. |
| 2005/0178494 A1 | 8/2005 | Schneider et al. |
| 2005/0215972 A1 | 9/2005 | Roe et al. |
| 2005/0215973 A1 | 9/2005 | Roe et al. |
| 2005/0249915 A1 | 11/2005 | Wood et al. |
| 2006/0069374 A1 | 3/2006 | Desai et al. |
| 2006/0155256 A1 | 7/2006 | Desai et al. |
| 2006/0212017 A1 | 9/2006 | Desai et al. |
| 2006/0271006 A1 | 11/2006 | Desai et al. |
| 2006/0271007 A1 | 11/2006 | Desai et al. |
| 2006/0292328 A1 | 12/2006 | Baldauf et al. |
| 2007/0088308 A1 | 4/2007 | Ehrnsperger et al. |
| 2007/0130732 A1 | 6/2007 | Matsumura et al. |
| 2007/0142798 A1 | 6/2007 | Goodlander et al. |
| 2007/0142806 A1 | 6/2007 | Roe et al. |
| 2007/0142815 A1 | 6/2007 | Macura et al. |
| 2007/0143972 A1 | 6/2007 | Kline et al. |
| 2007/0157441 A1 | 7/2007 | Kline et al. |
| 2007/0250026 A1 | 10/2007 | Venturino et al. |
| 2008/0021426 A1* | 1/2008 | Nakagawa et al. ........... 604/378 |
| 2008/0021432 A1 | 1/2008 | Kline et al. |
| 2008/0038507 A1 | 2/2008 | Seth et al. |
| 2008/0167635 A1 | 7/2008 | Kline et al. |
| 2009/0043273 A1* | 2/2009 | Carlucci et al. ............... 604/370 |
| 2009/0118689 A1 | 5/2009 | Lawson et al. |
| 2009/0264852 A1* | 10/2009 | Miyamoto et al. ........... 604/386 |
| 2009/0270826 A1 | 10/2009 | Shafer et al. |
| 2011/0040274 A1 | 2/2011 | Kline et al. |
| 2011/0056052 A1 | 3/2011 | Kline et al. |
| 2011/0056053 A1 | 3/2011 | Kline et al. |

FOREIGN PATENT DOCUMENTS

| | | | |
|---|---|---|---|
| JP | 2000/014702 A | | 1/2000 |
| JP | 2001/145663 A | | 5/2001 |
| JP | 2005/245555 A | | 9/2005 |
| WO | WO-94/14395 A1 | | 7/1994 |
| WO | WO-95/16746 A1 | | 6/1995 |
| WO | WO-95/24173 A2 | | 9/1995 |
| WO | WO-96/18367 A2 | | 6/1996 |
| WO | WO-01/87213 A1 | | 11/2001 |
| WO | WO-01/87214 A1 | | 11/2001 |
| WO | WO-01/87588 A2 | | 11/2001 |
| WO | WO-02/13747 A1 | | 2/2002 |
| WO | WO-03/082167 A2 | | 10/2003 |
| WO | WO-2004/030763 A2 | | 4/2004 |
| WO | WO-2004/082918 A2 | | 9/2004 |
| WO | WO 2005/016211 | | 2/2005 |
| WO | WO-2005/110731 A2 | | 11/2005 |
| WO | WO 2008143560 A1 | * | 11/2008 |

OTHER PUBLICATIONS

U.S. Appl. No. 13/034,795, filed Feb. 25, 2011, Donald Carroll Roe et al.

U.S. Appl. No. 13/034,800, filed Feb. 25, 2011, Donald Carroll Roe et al.

U.S. Appl. No. 13/034,816, filed Feb. 25, 2011, Donald Carroll Roe et al.

Office Actions and Responses for U.S. Appl. No. 11/638,988, filed Dec. 14, 2006 (63 pages).

Office Actions and Responses for U.S. Appl. No. 11/895,169, filed Aug. 23, 2007 (49 pages).

Office Actions and Responses for U.S. Appl. No. 11/638,748, filed Dec. 14, 2006 (51 pages).

Office Actions and Responses for U.S. Appl. No. 11/303,687, filed Dec. 16, 2005 (118 pages).

Office Actions and Responses for U.S. Appl. No. 11/971,973, filed Jan. 10, 2008 (21 pages).

International Search Report mailed Oct. 27, 2011.

* cited by examiner

ABSORBENT ARTICLE WITH IMPROVED GARMENT-LIKE CHARACTER

FIELD OF INVENTION

This invention relates to absorbent articles such as diapers having fastener bearing ears that yield a more garment-like article. The absorbent article may have improved functional characteristics and communicative properties.

BACKGROUND OF THE INVENTION

It has long been known that absorbent articles such as conventional taped diapers offer the benefit of receiving and containing urine and/or other bodily exudates. To effectively contain exudates, the article should provide a snug fit around the waist and legs of a wearer. Absorbent articles are known to have a chassis comprising a topsheet, a backsheet, and an absorbent core. Absorbent articles such as conventional taped diapers generally include a front and a rear waist section releasably and/or refastenably connected by a fastening system. The fastening system generally comprises an engaging member and a receiving member. The engaging member may be an adhesive tape, a hook bearing tape, a cohesive tape, or other like structure. The receiving member may be an element or zone on the article that may receive the engaging member such as a polymer film landing zone (viz., for receipt of the adhesive or cohesive tape) or a loop bearing surface (viz., for receipt of the hook bearing tape). The engaging member may be joined to the receiving member thereby interconnecting the rear waist section to the front waist section and thereby forming a waist opening and a pair of leg openings.

Current diaper designs frequently include the use of extensible ears. Back ears may extend laterally from the longitudinal edge of the rear waist section of the chassis. The engaging member of the fastening system may be attached to the back ear. In the case of front-fastened or taped designs, when the fastening system is engaged to the receiving member on the front waist region, the back ear serves as an interconnecting member between the front waist section and the rear waist section, which together form a waist opening and pair of leg openings. Back ears may be constructed to provide a degree of elastic recovery. Elasticized back ears allow the diaper to provide a more customized fit. Furthermore, the elastic capability allows the diaper to adjust to the forces exerted by the wearer without causing permanent deformation of the diaper or discomfort for the wearer of the diaper. Elasticity is typically imparted to the back ears by incorporating elastic materials into the ear. Due to the high cost of elastomeric materials, a common practice is to construct elastic ears as discrete components that are attached to the chassis (i.e., the main absorbent assembly to which other components may be disposed) resulting in a multipiece diaper. While this practice results in the efficient and cost-effective use of elastic materials, it is not without problems.

One problem seen in multipiece diapers is "tophatting." A "tophat" is a portion of the front or rear waist region that extends beyond the uppermost edge of the front or back ear toward the waist edge of the diaper. When a multipiece diaper is appropriately worn, the waist edge of the diaper in the front waist region and the rear waist region are substantially linear or slightly curvilinear. As the waist edge transitions from the rear waist region to the attached back ear, the waist edge may abruptly drop and then continue in a linear or curvilinear manner following the upper edge of the back ear. This "drop" from the waist edge in the front waist region or the rear waist region to the upper edge of the back ear may be one centimeter or greater. When worn, a taped diaper with the drop in the waist edge appears to have a notch cut from its side. The waist edge of such a diaper may have a stair step-like appearance.

Tophatting may have an adverse impact on the fit characteristics of a multipiece diaper. Generally, a diaper exerts a circumferential line of tension around a wearer's torso. This tension may be a product of the elastic back ear being strained. With a multipiece diaper exhibiting a tophat, the line of tension is located well below the waist edge because the line of tension is transmitted only along or through a continuous, unbroken path about the diaper. Since the tension-generating elasticized ear and fastening system are significantly remote from the waist edge, the line of tension is likewise remote from (e.g., generally lower than) the waist edge in the front waist region and rear waist region.

Fit and functionality problems may result from the line of tension being located remotely from the waist edge. For example, the front waist region and/or rear waist region of the diaper may exhibit sagging or fold-over. Sagging is the wrinkled, loose, gapped, or puckered configuration that the diaper exhibits when it is not under tension. Fold-over is the inversion of at least a portion of the diaper such that a body-facing surface of the diaper becomes garment-facing. Similar to sagging, fold-over may occur when the portion of the diaper is not under tension. Fold-over and sagging may also impair the gasketing function of the waist edge. For example, the interface of the waist edge and the wearer's waist is susceptible to leakage particularly when the wearer is in a prone or supine position. Fold-over and sagging can reduce the surface area of the diaper that is in close contact with the wearer at this interface which may result in leakage.

Furthermore, fold-over and sagging are aesthetically undesirable. Fold-over and sagging result in a diaper that is sloppy looking during wear. This, in turn, may communicate to the consumer that the diaper is of low quality which may be contrary to the high quality of functional characteristics such as absorbency or leakage prevention.

Top-hating and the resulting lack of a smooth, continuous, and circumferential waist edge communicate other unwanted messages to the consumer or wearer of the diaper. For example, tophatting may be a readily visible signal that the product is a diaper. For many wearers such as children being toilet trained or incontinent youths and adults, a stigma is attached to having to wear a diaper. To alleviate this concern, the diaper should communicate a message of being garment-like or underwear-like. In other words, it is desirable that the diaper not appear diaper-like. However, tophatting and discontinuous waist edges are apparent signals of a diaper.

Accordingly, it would be desirable to provide a diaper having a back ear that eliminates or reduces tophatting in a multipiece diaper. Furthermore, it is desirable that the diaper exhibit a smooth, continuous, circumferential waist edge without discontinuities or drops. It is desirable that the diaper exhibit a line of tension, which is provided at least in part by discrete ears, as close to the waist edge as possible. It is also desirable that the diaper communicate a message of being garment-like without the readily apparent visual cue (e.g., waist discontinuity) of being a diaper.

SUMMARY OF THE INVENTION

The present invention relates to a disposable absorbent article that comprises a chassis having a front region with a front edge, a rear region with a back edge, a crotch region between the front region and the rear region, and a pair of opposing longitudinal edges. The chassis comprises an absorbent core having front and back edges. The article also includes first and second elastically elongatable ears, each of the first and second ears having upper and lower edges and a transverse axis, each of the upper and lower edges having proximal and distal ends. The first and second ears define a back section of the absorbent article that is present between the back edge of the chassis and a line connecting the respective lower ends of the lower edge of the first and second ears. The article also includes first and second fastening tabs respectively connected the first and second elastically elongatable ears, each of the first and second fastening tabs having upper and lower edges and a transverse axis, each of the upper and lower edges having a proximal end. The back section of the absorbent article includes a portion of the absorbent core having an average caliper of less than about 1.5 mm and the first and second elastically elongatable ears are connected to the chassis such that the transverse axis of each of the first and second fastening tab is disposed between said back edge of the chassis and said back edge of said absorbent core.

DETAILED DESCRIPTION OF THE INVENTION

Figure 1A:
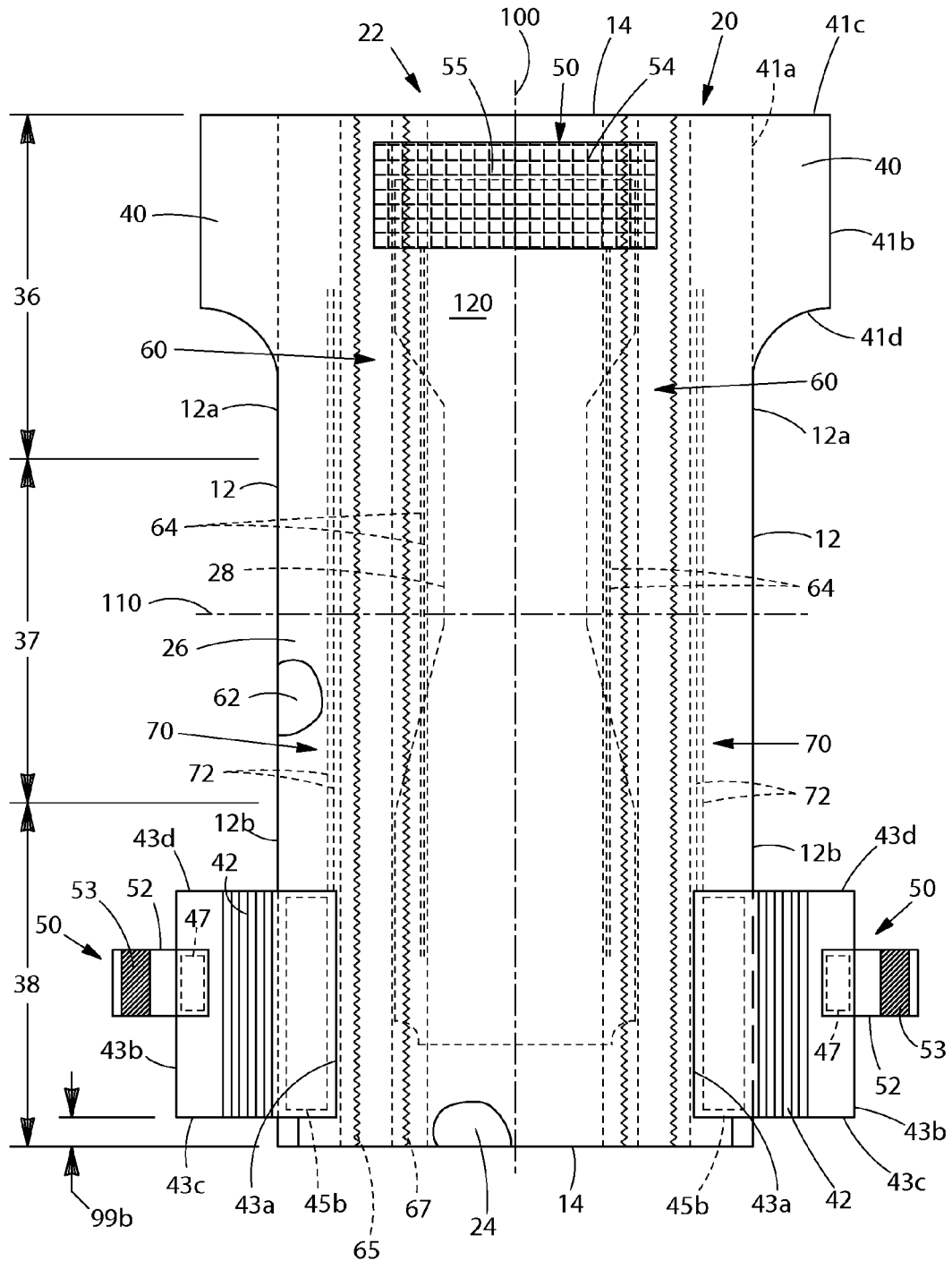
FIG. 1A is a plan view of an exemplary diaper in a flat, uncontracted state with back ears.

As used herein, the following terms shall have the meaning specified thereafter:

"Tophat" is a portion of a front or rear waist region of a diaper that extends beyond the uppermost edge of a front or back ear toward the waist edge of the diaper.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article, Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable." As is well known in the art, a common method for measuring the permeability to water, urine, or synthetic urine of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least 150% of its relaxed, original length (i.e. can stretch to 50% more than its original length), without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric. For example, an elastic material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a preformed waist and leg openings, A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Prefastened" refers to a disposable absorbent article that is manufactured such that the fastening system is in an engaged or fastened configuration.

"Consumer Commercial Good" refers to an item produced and distributed in large quantities and that the item may be purchased by a consumer through a retail establishment accessible to the public.

"Linear Projection" is the linear extension of an edge beyond the end point of the edge.

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of chassis 22 is defined by longitudinal edges 12 and lateral edges 14. The longitudinal edges 12 may be subdivided into a front longitudinal edge 12a, which is the portion of the longitudinal edge 12 in the front waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprises a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. A particularly topsheet 24 is available from BBA Fiberweb, Brentwood, Tenn. as supplier code 055SLPV09U.

Any portion of the topsheet 24 may be coated with a lotion as is known in the art. Examples of suitable lotions include those described in U.S. Pat. Nos., 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892, 536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. Non-limiting examples of suitable absorbent cores are described in greater details below.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964, Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially water-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The diaper 20 may include barrier cuffs 60 and/or gasketing cuffs 70. Gasketing cuffs 70 may also be referred to as outer leg cuffs, leg bands, side flaps, leg cuffs, or elastic cuffs. Barrier cuffs 60 may also be referred to as second cuffs, inner leg cuffs or "stand-up" elasticized flaps.

The gasketing cuff 70 may be substantially inelastic or may be elastically extensible to dynamically fit at the wearer's leg. The gasketing cuff 70 may be formed by one or more elastic members 72 (such as elastic strands) operatively joined to the topsheet 24, backsheet 26, or any other suitable substrate used in the formation of the diaper 20. Suitable gasketing cuff construction is further described in U.S. Pat. No. 3,860,003

The barrier cuff 60 may span the entire longitudinal length of the diaper 20. The barrier cuff 60 may be formed by a flap 62 and an elastic member 64 (such as elastic strands). The flap 62 may be a continuous extension of any of the existing materials or elements that form the diaper 20. In other embodiments, such as shown in FIG. 1, the barrier cuff 60 may be a discrete element. In such embodiments, the barrier cuff 60 comprising the flap 62 and the elastic member 64 may be formed then joined to the chassis 22 by a bond 65.

The flap 62 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap 62 may comprise a nonwoven web such as spunbond webs, meltblown webs, carded webs, and combinations thereof (e.g., spunbond-meltblown composites and variants). Laminates of the aforementioned substrates may also be used to form the flap 62. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having barrier cuffs and suitable construction of such barrier cuffs may be found in U.S.

Pat. Nos. 4,808,178 and 4,909,803. The elastic member 64 may span the longitudinal length of the barrier cuff 60. In other embodiments, the elastic member 64 may span at least the longitudinal length of the barrier cuff 60 within the crotch region 37. It is desirable that the elastic member 64 exhibits sufficient elasticity such that the barrier cuff 60 remains in contact with the wearer during normal wear, thereby enhancing the barrier properties of the barrier cuff 60. The elastic member 64 may be connected to the flap 62 at opposing longitudinal ends. In certain embodiments, the flap 62 may be folded over onto itself so as to encircle the elastic member 64. A bond 67 may be used to secure the folded section of the flap 62.

The barrier cuffs 60 and/or gasketing cuffs 70 may be treated, in full or in part, with a lotion, as described above with regard to topsheets, or may be fully or partially coated with a hydrophobic surface coating as detailed in U.S. application Ser. No. 11/055,743, which was filed Feb. 10, 2005.

The diaper 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In certain embodiments the ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the side panel are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two nonwoven layers (such as is available from BBA. Fiberweb, Brentwood, Tenn. as supplier code FPN332).

The ears 40, 42 may be discrete or integral. A discrete ear is formed as separate element which is joined to the chassis 22. An integral ear is a portion of the chassis 22 that projects laterally outward from the longitudinal edge 12, The integral ear may be formed by cutting the chassis form to have the projection.

Figure 1B:
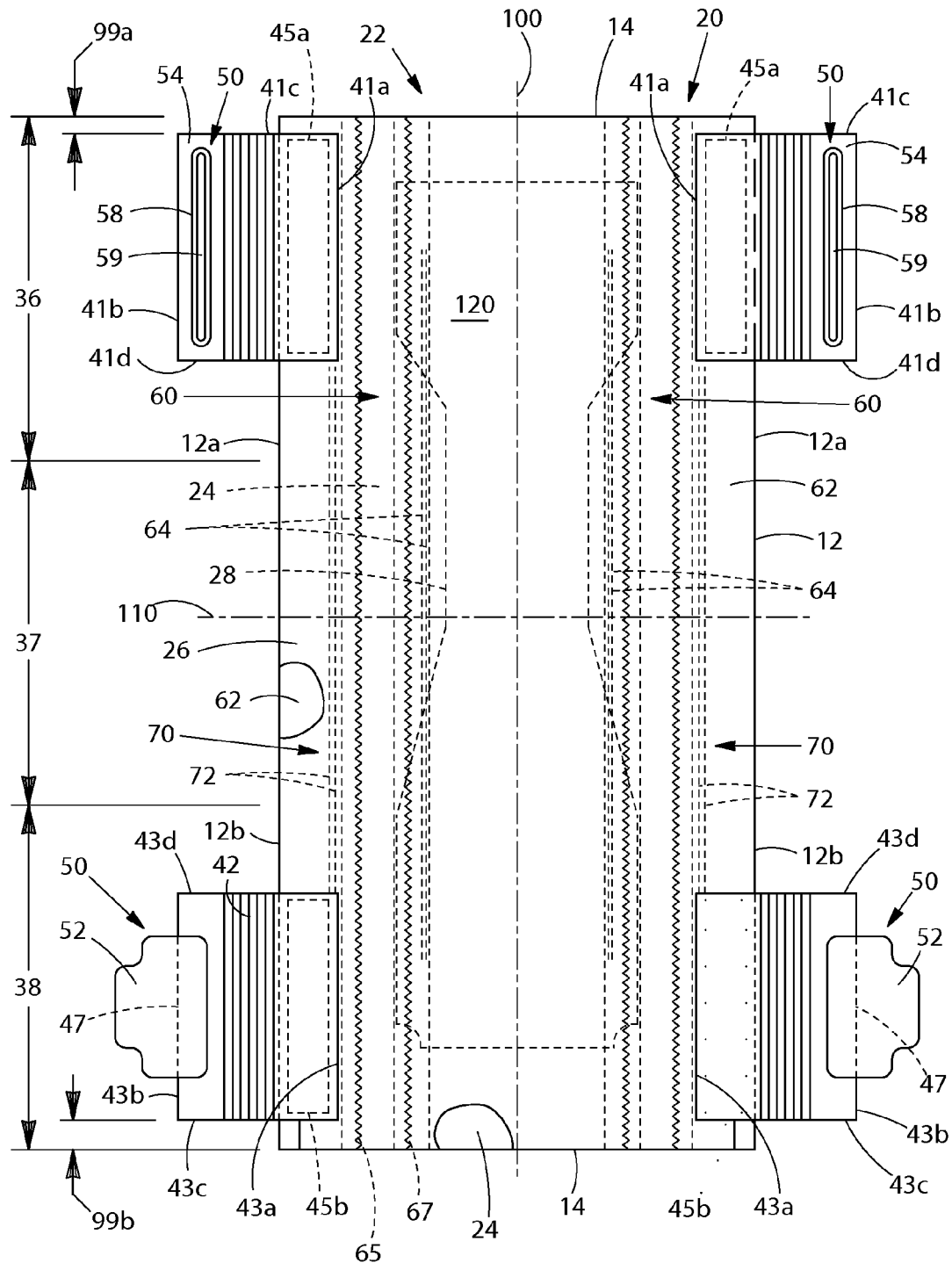
FIG. 1B is a plan view of an exemplary diaper in a flat, uncontracted state with front ears and back ears.

A suitable diaper 20 having discrete back ears 42 and integral front ears 40 is shown in FIG. 1A. A suitable diaper having discrete back ears 42 and discrete front ears 40 is shown in FIG. 1B, The front ears 40 may have a proximal edge 41a, a distal edge 41b, an upper edge 41c, and a lower edge 41d. A portion of the front ear 40 adjacent to the proximal edge 41a may be joined to the chassis 22 at a front bond region 45a. The front bond region 45a is the area within which one or more bonds join the discrete front ear 40 to the chassis 22. The front bond region 45a may comprise one or more bonds formed by any bonding method known in the art such as adhesive bonding, pressure bonding, heat bonding, and the like. If the front bond region 45a comprises more than one bond, such as in an array or pattern of bonds, the front bond region 45a is defined by the are bounded by a polygon connecting the outermost bonds in each dimension. There may be a degree of overlap between the front ear 40 and the chassis 12 to allow for bonding. However, in other embodiments, a larger portion of the front ear 40 may comprise a layer, element, or substrate of the chassis 22.

Figure 1C:
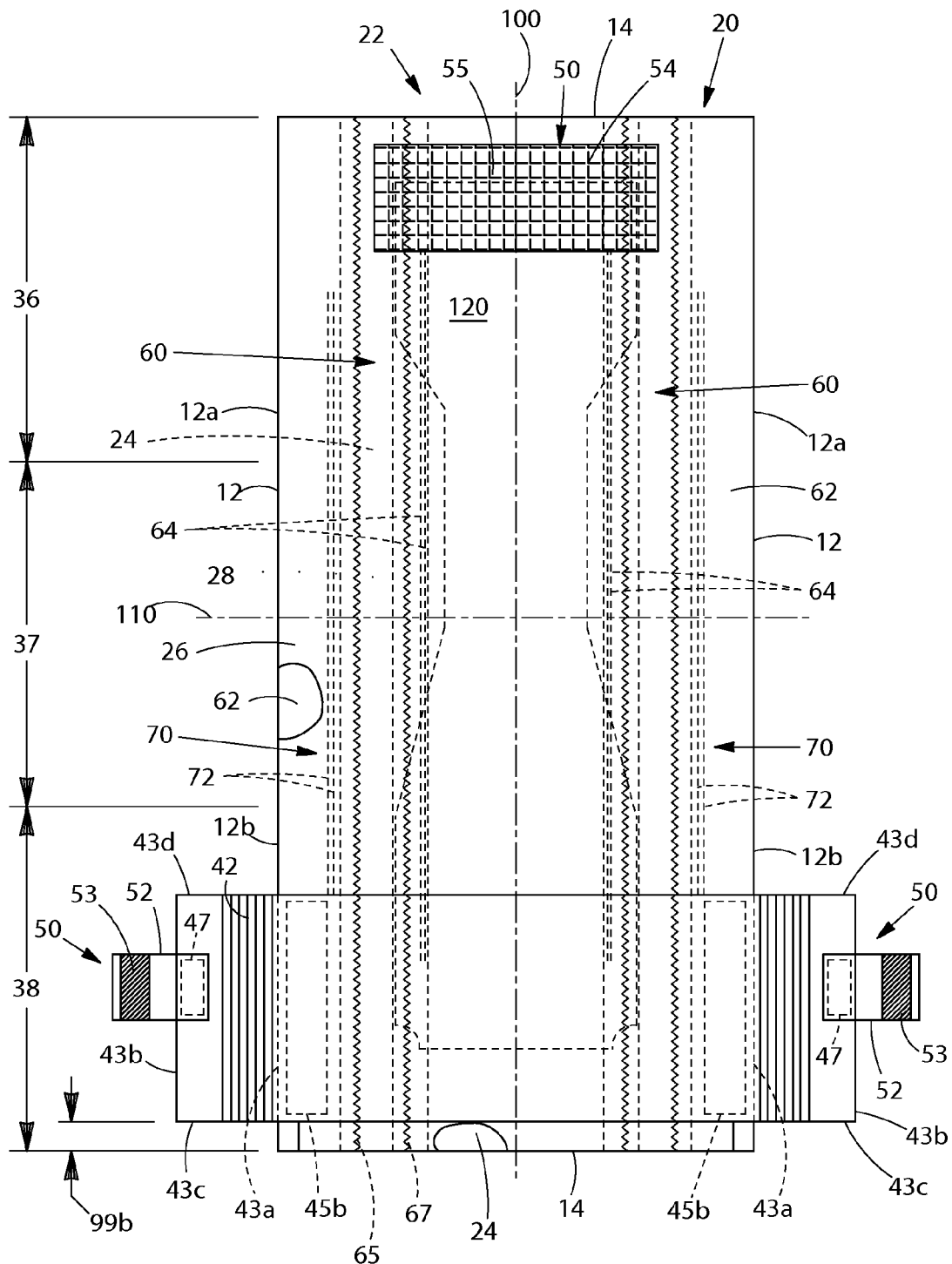
FIG. 1C is a plan view of an exemplary diaper in a flat, uncontracted state with back ears formed by a belt.

FIG. 1C depicts an embodiment of a diaper 20 having a belt 49 that forms both back ears 42. In this embodiment, no front ears are present. The belt 49 may extend beyond the opposing longitudinal edges 12. The back ears 42 may have a proximal edge 43a, a distal edge 43b, an upper edge 43c, and a lower edge 43d. The proximal edge 43a is taken as projection of the longitudinal edge 12 on the belt 49.

As shown in both FIGS. 1A-C, the back ear 42 may be a discrete element or a portion of a discrete element (e.g., the belt 45) that is joined to the chassis 22. The back ears 42 may have a proximal edge 43a, a distal edge 43b, an upper edge 43c, and a lower edge 43d. A portion of the back ear 42 adjacent to the proximal edge 43a may be joined to the chassis 22 at a back bond region 45b. The back bond region 45b is the area within which one or more bonds join the back ear 42 to the chassis 22. The back bond region 45b may comprise one or more bonds formed by any bonding method known in the art such as adhesive bonding, pressure bonding, heat bonding, and the like. If the back bond region 45b comprises more than one bond, such as in an array or pattern of bonds, the back bond region 45b is defined by the are bounded by a polygon connecting the outermost bonds in each dimension. There may be a degree of overlap between the back ear 42 and the chassis 12 to allow for bonding. However, in other embodiments, a larger portion or all of the back ear 42 may comprise a layer, element, or substrate of the chassis 22.

The diaper 20 may also include a fastening system 50. When fastened, the fastening system 50 interconnects the front waist region 36 and the rear waist region 38 resulting in a waist circumference that may encircle the wearer during wear of the diaper 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1A depicts a fastening system 50 having an engaging member 52 proximate the distal edge 43b of the back ear 42 and a receiving member 54 disposed in the front waist region 36 of the chassis 22. The engaging member 52 is shown having an engaging surface 53 that may comprise hooks, loops, an adhesive, a cohesive, or other fastening member. FIG. 1A depicts the engaging surface 53 as covering only a portion of the engaging member 52; however, in other embodiments, the engaging surface 53 may cover substantially all of one or more faces of the engaging member 52. The engaging member 52 may be joined to the back ear 42 at a fastener bond region 47. The fastener bond region 47 is the area within which one or more bonds join the engaging member 52 to the back ear 42. The fastener bond region 47 may comprise one or more bonds formed by any bonding method known in the art such as adhesive bonding, pressure bonding, heat bonding, and the like. If the fastener bond region 47 comprises more than one bond, such as in an array or pattern of bonds, the fastener bond region 47 is defined by the are bounded by a polygon connecting the outermost bonds in each dimension. In certain cases, such as shown in FIG. 1B, the fastener bonding region 47 may be a line of attachment.

The receiving member 54 may have a receiving surface 55 (as shown in FIGS. 1A and 1C) that allows for engagement of the engaging member 52. The receiving surface 54 may comprise hooks, loops, an adhesive, a cohesive, or other fastening component that can receive the engaging member 52, Suitable engaging member 52 and receiving member 54 combinations include but are not limited to hooks/loop, hooks/hooks, adhesive/polymeric film; cohesive/cohesive, adhesive/adhesive; tab/slot; and button/button hole.

Figure 2A:
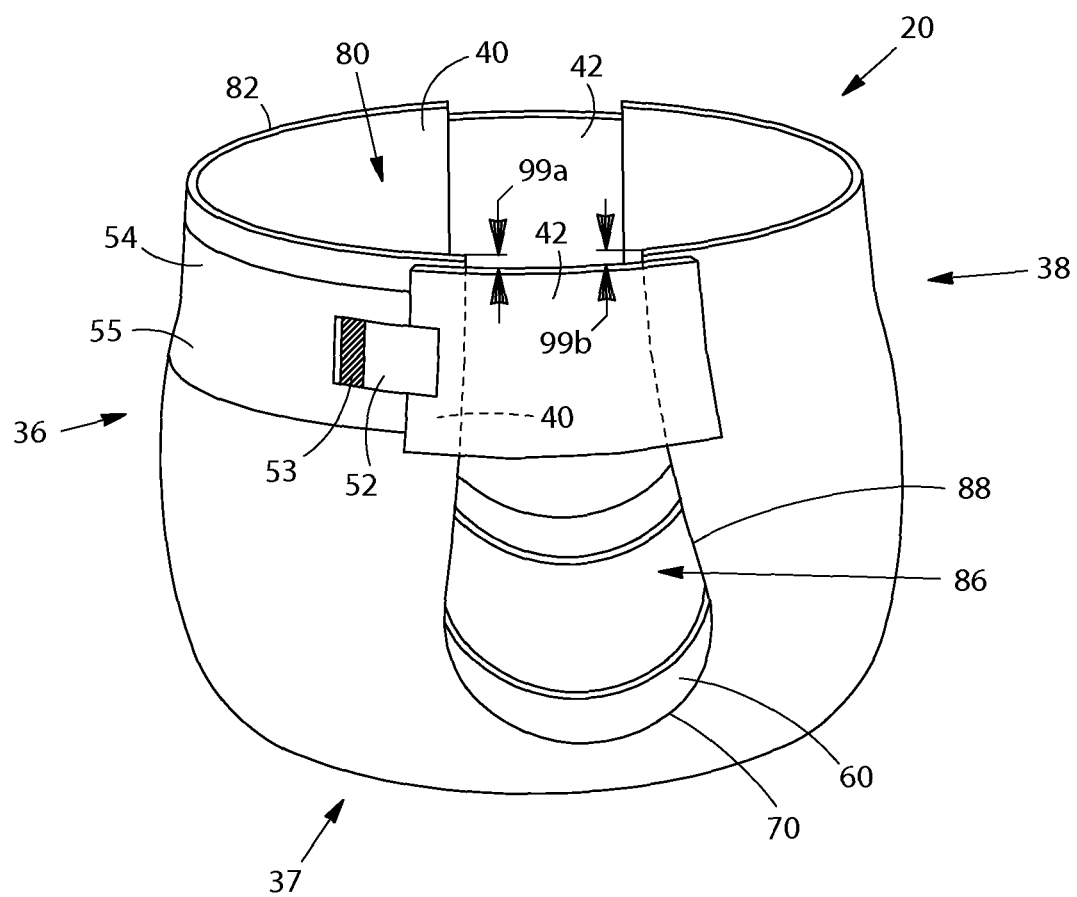
FIG. 2A is a perspective view of the diaper of FIG. 1A in a fastened configuration as would be exhibited during wear.

FIG. 2A is a perspective view of the diaper 20 of FIG. 1A in a fastened configuration as would be seen during normal wear of the diaper. The engaging surface 53 of the engaging member 52 may be mated with the receiving member 54. The back ear 42 may span and connect the front waist region 36 and the rear waist region 38 to form a leg opening 86 defined by a leg edge 88 (which includes a portion of the longitudinal edge 12 and the lower edge 44*d* of the back ear 42) and a waist opening 80 defined by a waist edge 82 (which includes a portion of the lateral edges 14 of the chassis 22 and the upper edge 44*c* of the back ear 42). In embodiments where the back ear 42 is extensible or elastic, the back ear 42 may be extended to provide a tensioning force to the diaper 20 during wear.

Figure 2B:
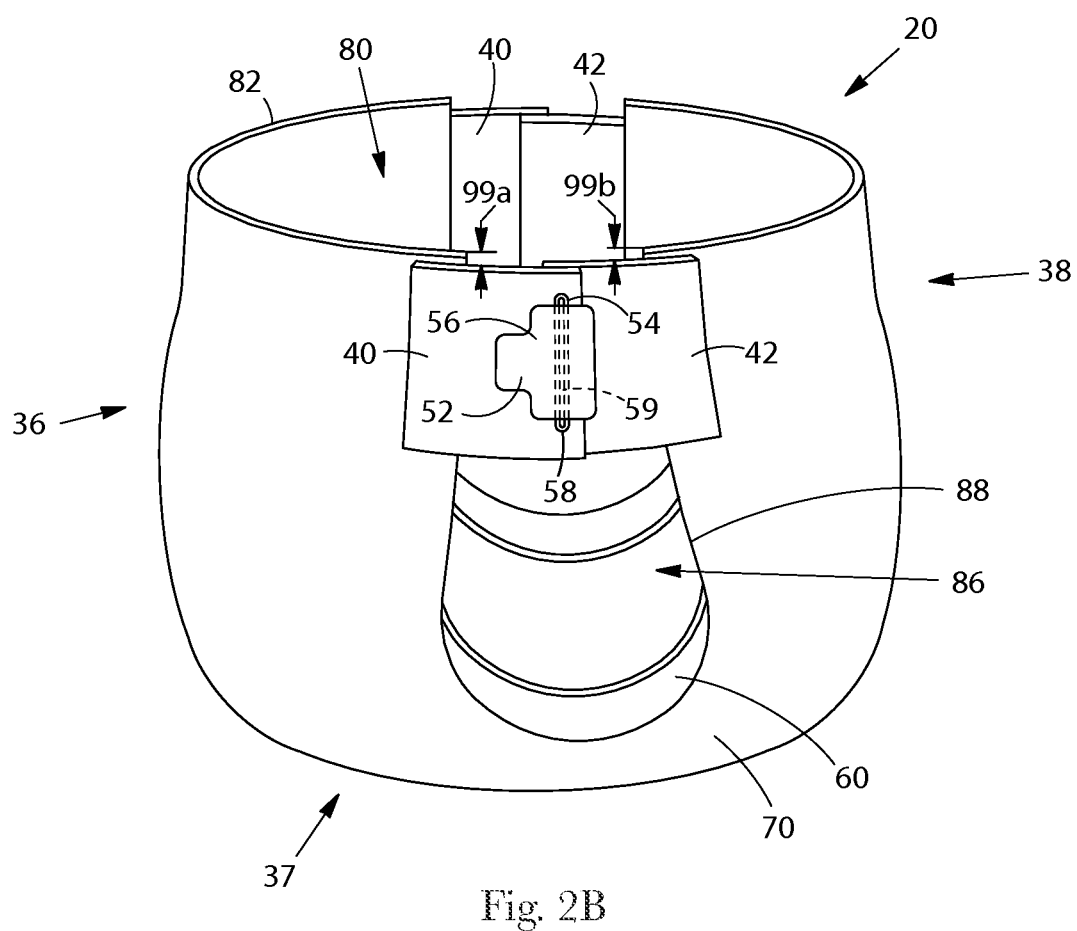
FIG. 2B is a perspective view of the diaper of FIG. 1B in a fastened configuration as would be exhibited during wear.

FIG. 1B depicts a diaper 20 having front and back ears 40, 42. The diaper may have a fastening system 50 comprising an engaging member 52 and a receiving member 54. The engaging member 52 may be disposed proximate the distal edge 43*b* of the back ear 42. The receiving member 54 may be disposed proximate the distal edge 41*b* of the front ear. In the FIG. 1B, the engaging member 52 is depicted as a tab member 56 and the receiving member 54 is depicted as a slot member 58 with a slot 59 therethrough. In a simple form, the fastening system 50 may be fastened by passing the tab member 56 completely through the slot 59 of the slot member 58. Once the tab member 56 has been passed through the slot member 58, the tab member 56 may be rotated into a plane generally parallel with the plane of the slot member 58 such that at least a part of the tab member 56 overlaps at least a portion of the slot member 58, FIG. 2B is a perspective view of the diaper 20 of FIG. 1B in a fastened configuration as would be seen during normal wear of the diaper 20. The tab member 56 and the slot member 58 are joined to form a leg opening 86 defined by a leg edge 88 (which includes a portion of the longitudinal edge 12, the lower edge 41*d* of the front ear 40, and the lower edge 43*d* of the back ear 42) and a waist opening 80 defined by a waist edge 82 (which includes a portion of the lateral edges 14 of the chassis 22, the upper edge 41*c* of the front ear, and the upper edge 43*c* of the back ear 42). In embodiments where the front ear 40 or the back ear 42 is extensible or elastic, the ear 40, 42 may be extended to provide a tensioning force to the diaper 20 during wear. It should be recognized that other suitable engaging member 52 and receiving member 54 combinations may be used instead or in addition to the tab and slot.

FIGS. 1A-C and 2A-B include as front tophat 99*a* and/or a back tophat 99*b*. In FIG. 1A, the back tophat 99*b* is shown in the rear waist region 38 as the portion of the diaper 20 bounded by the upper edge 43*c* of the back ear 42 and the lateral edge 14 in the rear waist region 38. Once fastened, as shown in FIG. 2A, the diaper 20 may have a front tophat 99*a* in the front waist region 36. The front tophat 99*a* is the portion of the diaper 20 bounded by the upper edge 41*c* of the back ear 42 and the lateral edge 14 in the front waist region 36.

In FIGS. 1B and 2B, the front tophat 99*a* is shown in the front waist region 36 as the portion of the diaper 20 bounded by the upper edge 41*c* of the front ear 40 and the lateral edge 14 in the front waist region 36. The back tophat 99*b* is shown in the rear waist region 38 as the portion of the diaper 20 bounded by the upper edge 43*c* of the back ear 42 and the lateral edge 14 in the rear waist region 38.

In FIG. 1C, the back tophat 99*b* is shown in the rear waist region 38 as the portion of the diaper 20 bounded by the upper edge 43*c* of the back ear 42 and the lateral edge 14 in the rear waist region 38.

Figure 3A:
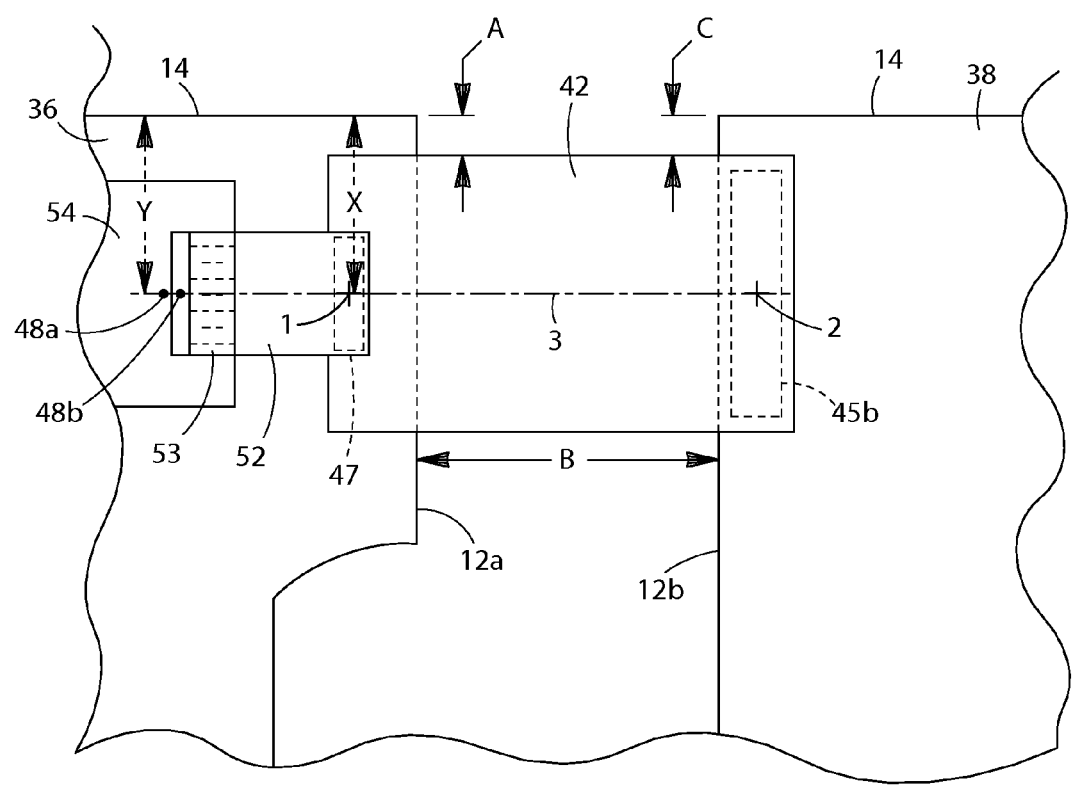
FIG. 3A is a magnified planar, side view of the diaper of FIG. 2A.
Figure 3B:
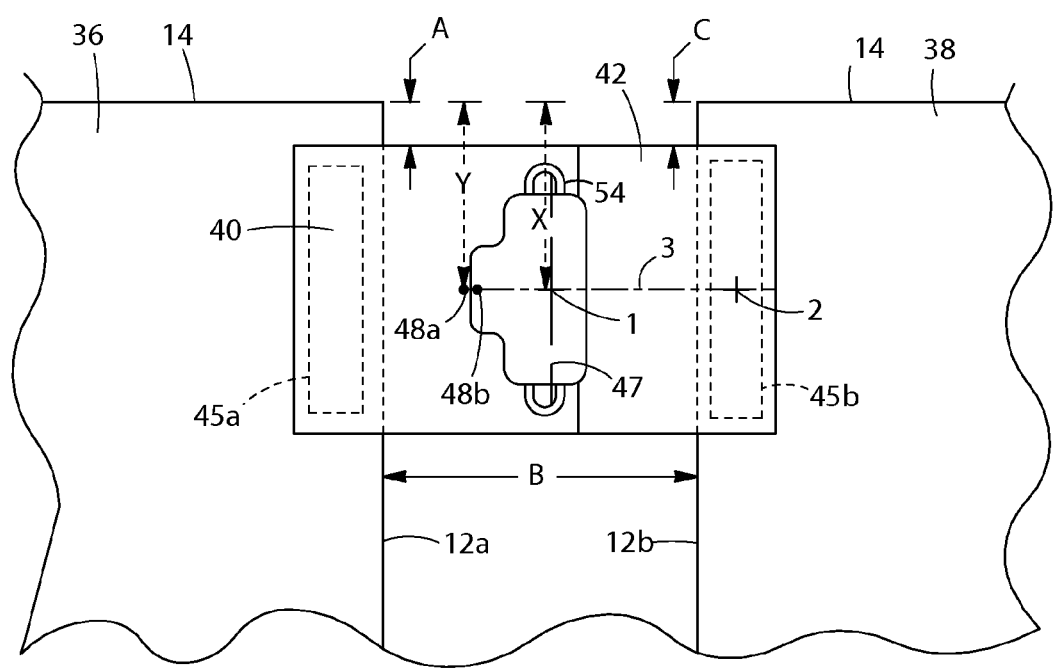
FIG. 3B is a magnified planar, side view of the diaper of FIG. 2B.

FIG. 3A is a magnified planar, side view of the diaper 20 of FIG. 2A showing the back ear 42, a portion of the front waist region 36, and a portion of the rear waist region 38. FIG. 3B is a magnified planar, side view of the diaper 20 of FIG. 2B showing the back ear 42, the front ear 40, a portion of the front waist region 36, and a portion of the rear waist region 38. To more precisely and quantitatively describe the tophats 99*a* and 99*h*, a number of metrics are shown. Suitable metrics include a Front Edge Displacement A, a Rear Edge Displacement C, an Ear Span Width B, an Ear Midpoint Width X, and a Receiving Member Midpoint Width Y. Several of the metrics are determined with reference to a first product mark 1, a second product mark 2, and a lateral reference line 3. The receiving member 54 may include a longitudinal midpoint 48*a*. The engaging member may include a longitudinal midpoint 48*b*. The method for measuring the metrics and applying the product marks 1 and 2, the lateral reference line 3, the midpoints 48*a*, 48*b* to the diaper 20 is discussed below in the Metric Test Method section.

To address the problem of tophatting, it is desirable that the Front Edge Displacement A and the Rear Edge Displacement C be reduced or eliminated. In certain embodiments, the Front Edge Displacement A may be no greater than about 1.0 mm. Alternatively, the Front Edge Displacement A may be no greater than about 0.5 mm or about 0.3 mm. In certain embodiments, the Front Edge Displacement A may be about 0. In certain embodiments, the Rear Edge Displacement C may be no greater than about 10 mm. Alternatively, the Rear Edge Displacement C may be no greater than about 7 mm, about 5 mm, about 3 mm, or about 1 mm. In certain embodiments, the Rear Edge Displacement C may be about 0. Any combination of the aforementioned Front Edge Displacement A and Rear Edge Displacement C is also within the scope of the invention. Furthermore, in certain embodiments, the sum of the Front Edge Displacement A and the Rear Edge Displacement C may be no greater than about 12 mm. Alternatively, the sum of the Front Edge Displacement A and the Rear Edge Displacement C may be no greater than about 10 mm, about 5 mm, about 3 mm, or about 1 mm. In certain embodiments, the sum of the Front Edge Displacement A and the Rear Edge Displacement C may be about 0.

In other embodiments, it has been found that a ratio of the Front Edge Displacement A or Rear Edge Displacement C to the Ear Span Width B is very important in consumer perception of tophatting and the resulting waist edge discontinuity. For example, the waist edge discontinuity may be less appreciable in a diaper with a larger Ear Span Width B rather than with a diaper having a smaller Ear Span Width B. In certain embodiments, the ratio of the Front Edge Displacement A to the Ear Span Width B (A/B) may be no greater than about 0.05. In certain embodiments, the ratio of the Front Edge Displacement A to the Ear Span Width B (A/B) is about 0. In certain embodiments, the ratio of the Rear Edge Displacement C to the Ear Span Width B (CB) may be no greater than about 0.24. Alternatively, the ratio of the Rear Edge Displacement C to the Ear Span Width B (C/B) may be no greater than about 0.20 or about 0.10. In certain embodiments, the ratio of the Rear Edge Displacement C to the Ear Span Width B (CM) is about 0.

In other embodiments, it may be desirable that the combined Front Edge Displacement A and the Rear Edge Displacement C be minimized in relation to the Ear Span Width B. The sum of Front Edge Displacement A and the Rear Edge Displacement C to the Ear Span Width B ratio ((A+C)/B) may be no greater than about 0.30. Alternatively, the combined Front Edge Displacement A and the Rear Edge Displacement C to the Ear Span Width B ratio ((A+C) B) may be less than about 0.20 or about 0.10. In other embodiments, the combined Front Edge Displacement A and the Rear Edge Displacement C to the Ear Span Width B ratio ((A+C)/B) is about 0.

In other embodiments, it has been found that a ratio of the Front Edge Displacement A to the Ear Midpoint Width X is very important in consumer perception of tophatting and the resulting waist edge discontinuity. For example, the waist edge discontinuity may be less appreciable in a diaper with a larger Ear Midpoint Width X rather than with a diaper having a smaller Ear Midpoint Width X. In certain embodiments, the ratio of the combined Front Edge Displacement A and the Rear Edge Displacement C to the Ear Midpoint Width X ((A+C)/X) may be less than about 0.30. Alternatively, the ratio of the combined Front Edge Displacement A and the Rear Edge Displacement C to the Ear Midpoint Width X ((A+C)/X) may be about 0.25, about 0.20, or about 0.10. In other embodiments, the ratio of the combined Front Edge Displacement A and the Rear Edge Displacement C to the Ear Midpoint Width X ((A+C)/X) is about 0.

FIGS. 1-3 depict the back ear 42 being bonded to and extending from the rear waist region 38 and designed such that the engaging member 52 joined to the back ear 42 may engage the receiving member 54 disposed in the front waist region 36. However, it should be readily apparent to one skilled in the art that the back ear may be configured to be a front ear 42 which may be bonded to and extend from the front waist region 36 and designed such that the engaging member 52 joined to the front ear may engage the receiving member 54 disposed in the rear waist region 38. The Front Edge Displacement A, Rear Edge Displacement C, Bar Span Width B, Ear Midpoint Width X, and the Receiving Member Midpoint Width. Y are equally applicable to a front ear.

Metric Test Method

This method describes a method to mark and capture physical reference points on diapers as they are pulled to known tensile force values with a calibrated programmable mechanical tensile tester. This method also describes the process for making the appropriate distance calculations using spreadsheet software such as Microsoft Excel. These calculations are based upon measurements of pixel x-y coordinates taken from digital camera images through the use of photoanalysis computer program.

Figure 4:
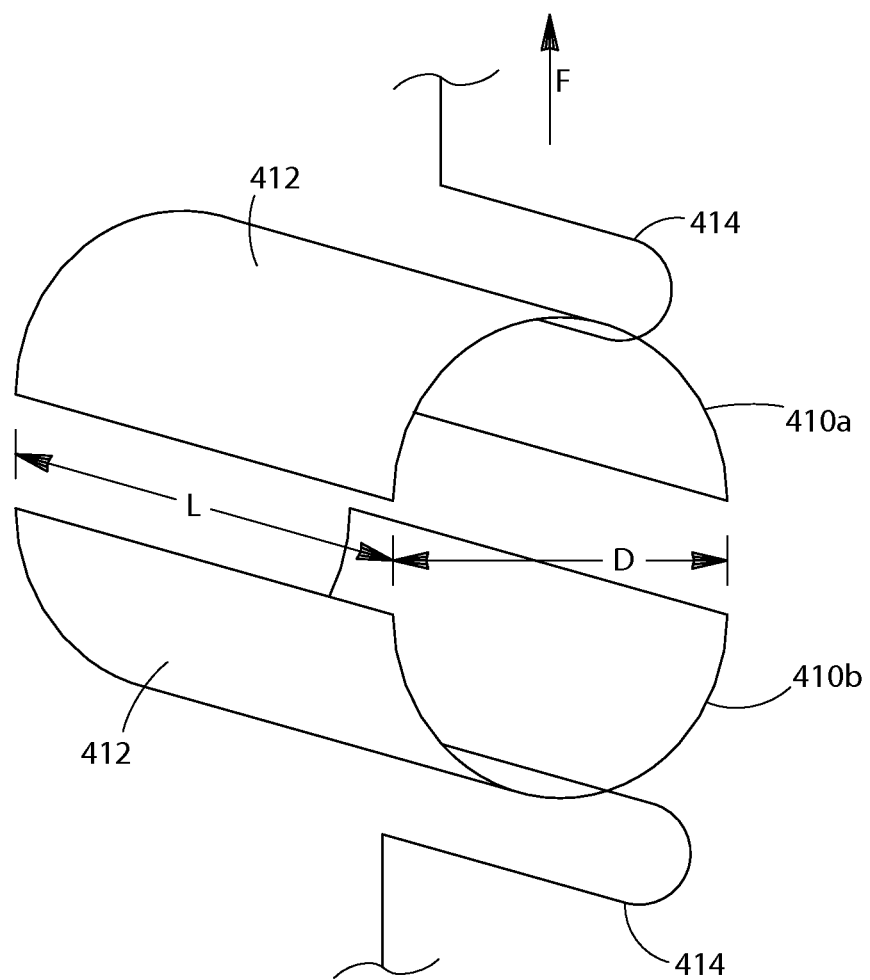
FIG. 4 is a perspective view of a suitable grip for use in the Metric Test Method.

A suitable tensile tester must be capable of pulling at a constant crosshead rate of 127 mm/min. The tensile tester must be equipped with a calibrated load cell such that the tested load values are no less than 1% of the calibration ranged of the load cell. A suitable tensile tester is a MTS Tensile Tester, Model 1/S available from MTS Systems Corp., Eden Prairie, Minn. and loaded with a ION load cell. The tensile tester includes two matching grips 410a and 410b as shown in FIG. 4. Each grips 410a, 410b includes a semi-cylindrical face 412 upon which a sample may be mounted. The faces 412 are made from 1.50 mm thick stainless having a length L of 127 mm. The faces 412 have a diameter D of 115 mm. Each face 412 is joined to a hook 414 that allow the grip 410 to be joined to the tensile tested. The hook 414 runs the length L of the inside surface of the semi-cylindrical face. One grip 410a is joined to the load cell and movable crosshead of the tensile tester. The other grip 410b is joined to the non-moving base of the tensile tester.

All values reported below are an average of five random samples. To ensure the randomization of consumer commercial samples, the five samples are to be taken as follows:
  (i) If the consumer commercial sample is sold individually (i.e., one sample may be individually purchased), then five consumer commercial samples are acquired.
  (ii) If the consumer commercial sample is to be sold as a plurality (i.e., several samples are purchased as a single unit), then five pluralities are to be acquired. One sample from each of the five pluralities is randomly chosen for testing.

Product Marks:

Two product marks "+" are to be placed on the left side (i.e., the side of the product that would fall along the left side of a wearer during normal wear of the sample) of each sample prior to testing. The product marks may be made using a fine tip permanent marker or like device. The first product mark 1, as shown in FIGS. 3A-B, is made according to the following steps:
  1. If the product has a fastener bonding zone 47 (as shown in FIG. 3A-B), the first product mark is placed in the center of the fastener bonding zone 47.
  2, if the product has no fastener bonding zone 47, the first product mark is placed in the center of the engaging surface 53.
  3. If 1 or 2 are not available, the first product mark is placed in the center of the engaging member 52.

The second product mark 2, as shown in FIGS. 3A-B, is placed in the center of the back bond region 45b. A lateral reference line 3 is drawn through the first product mark 1 and the second product mark 2; the line 3 terminates at the inboard and outboard edge of the car/engaging member combination.

Figure 5A:
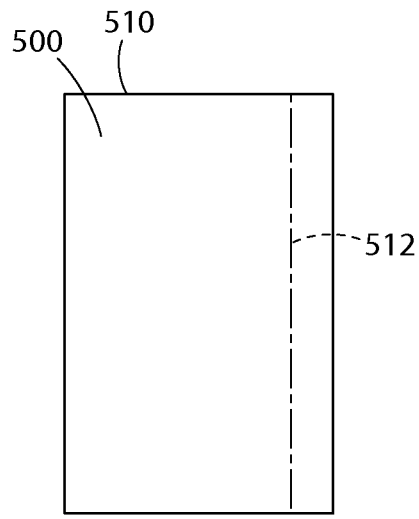
FIGS. 5A-C depict suitable edge determinations.

Metric Measurement:

The Front Edge Displacement A, Rear Edge Displacement C, Ear Span Width B, Ear Midpoint Width X, and the Receiving Member Midpoint Width Y may be determined according to the description provided below and with reference to FIGS. 3A-B. For purposes of metric measurement and procedural steps, when measuring to or from an edge, the term "edge" means in order of preference:
  1. A physical edge 510 of a sample 500 if said edge 510 is linear and intersects with a line segment 512 to be drawn, as shown in FIG. 5A,
  2. If not 1, then a linear projection 514 from the physical edge 510 of the sample 500 if the physical edge 510 is substantially linear, as shown in FIG. 5E.
  3. If not 1 or 2, then a tangential line 516 drawn from the outermost point 518 on the physical edge 510 of the sample 500, as shown in FIG. 5C.

Figure 5B:
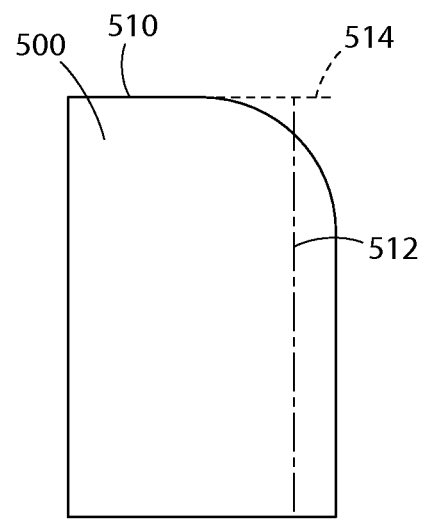
Figure 5C:
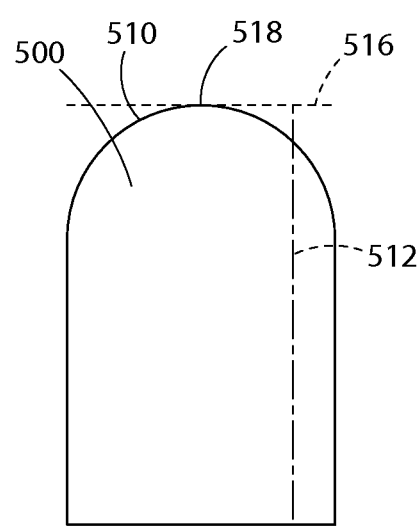

FIGS. 5A-C are provided to teach how the linear projection and tangential line should be drawn on a simple shape (e.g., sample 500). One skilled in the art will be able to apply these teachings to drawing the linear projection and tangential line on the various edges of an absorbent article.

The Front Edge Displacement A is the distance of a line segment drawn from (i) the intersection of the upper edge of the ear and the front longitudinal edge 12a and perpendicular to (ii) the lateral edge 14 in the front waist region 36, a linear projection of the lateral edge 14 in the front waist region 36, or, for samples where there is no linear component of the edge, a tangent line drawn from the edge. As shown in FIG. 3A, the Front Edge Displacement A is the distance between the upper edge 43c of the back ear 42 and the lateral edge 14 of the front waist region 38. As shown in FIG. 3B, the Front Edge Displacement A is the distance between the upper edge 41c of the front ear 40 and the lateral edge 14 of the front waist region 38.

The Rear Edge Displacement C is the distance of a line segment drawn from (i) the intersection of the upper edge of the ear and the rear longitudinal edge 11b and perpendicular to (ii) the lateral edge 14 in the rear waist region 38 or a linear projection of the lateral edge 14 in the rear waist region 38. As shown in FIGS. 3A and 38, the Rear Edge Displacement C is the distance between the upper edge 44c of the back ear 42 and the longitudinal edge 14 of the rear waist region 38.

The Ear Span Width B is the linear distance of a line segment drawn from (i) the intersection of the lower edge of a back ear with either the front longitudinal edge 12a or an edge of the front ear 40, whichever is most outboard and (ii) the intersection of the rear longitudinal edge 12b and a lower edge of a back ear. As shown in FIG. 3A, the Ear Span Width B is the distance between (i) the intersection of the front longitudinal edge 12a and the lower edge 43d of the back ear 42 and (ii) the intersection of the rear longitudinal edge 12b and the lower edge 43d of the back ear 42. However, for side fastened diapers, such as shown in FIG. 3B, the Ear Span Width B is the distance of a line segment drawn from (i) the intersection of the front longitudinal edge 12a and the lower edge 41d of the front ear 40 and (ii) the intersection of the rear longitudinal edge 12b and the lower edge 43d of the back ear 42.

The Ear Midpoint Width X is the distance of the line segment drawn from (i) the first product mark 1 and perpendicular to (ii) the lateral edge 14 in the front waist region 36 or a linear projection of the lateral edge 14 in the front waist region 36.

The Receiving Member Midpoint Width Y is the distance of the line segment drawn from (i) a midpoint 48 of the receiving member 54 adjacent the inboard edge of the engaging member 52 (when the receiving member 54 and the engaging member 52 are in a fastened configuration) and perpendicular to (ii) the lateral edge 14 in the front waist region 36 or a linear projection of the lateral edge 14 in the front waist region 36. The longitudinal midpoint 48 of the receiving member 54 is the midpoint of a line segment drawn longitudinally from opposing lateral edges of the receiving member 54. In some instances such as shown in HG, 3B, the receiving member 54 may be overlapped by the engaging member 52. In such instances, the midpoint 48 of the receiving member 54 is the midpoint of a line segment drawn longitudinally from the linear projection of the opposing lateral edges of the receiving member 54 and drawn adjacent to the inboard edge of the engaging member 52.

Procedural Steps:

The metrics are measured according to the steps that follow:

1. A calibration ruler is placed in proximity to the grips. The calibration ruler marked in millimeters is mounted so the ruled-face of the ruler is on the same plane as the surface of the product being measured.
2. A digital camera is mounted on a tripod adjacent to the tensile tester and positioned in such a way that the sample and calibration ruler fill the camera's field of view as much as possible. The camera is aligned vertically and horizontally with the surface of the sample.
3. The sample is marked with the two product marks and the lateral reference line as described above,
4. The sample is fastened to the sample's largest possible fastener setting. The engaging member should be joined to the receiving member such that a longitudinal midpoint of the engaging member is aligned longitudinally, at the point of intersection, with a longitudinal midpoint of the receiving member. The longitudinal midpoint of the receiving member is the midpoint of a line segment drawn longitudinally from opposing lateral edges of the receiving member. The longitudinal midpoint of the engaging member is the midpoint of a line segment drawn longitudinally from opposing lateral edges of the engaging member. Additionally, the proximal edge of the engaging surface should be aligned with the longitudinal edge of the receiving surface. In samples not having a distinct engaging surface or receiving surface, the engaging member and receiving member of the sample should be fastened such that (i) the lateral edges in the front and back waist regions are aligned and (ii) the distal edge of the engaging member is placed 50 mm inboard of the longitudinal edge of the front waist region or as far outboard as possible while still maintaining engagement to the front waist region, whichever results in the fastener being closer to the longitudinal edge of the front waist region.
5. The sample is mounted onto the grips of the tensile tester such that the front waist region of the sample is approximately centered on the movable grip and that the back waist region of the sample is approximately centered on the stationary grip. The sample is mounted sample so that the sample marks are facing the camera, all test values are visible, the sample is at the same distance from the camera as the ruler, and the sample is perpendicular to the camera's field or view.
6. The sample is pulled at a constant crosshead rate of 127 mm/min and held in position for 10 seconds when the load reaches 200 grams. A picture is taken.
7. The sample is pulled at a constant crosshead rate of 127 mm/until a load value of 1200 grams is reached. The crosshead is stopped and a picture is taken.
8. The crosshead is returned to the original position.

Using a computer imaging program capable of displaying pixel values in pictures (i.e., Adobe® Photoshop®), each picture taken at 1200 g load is analyzed. For each picture, a line is drawn on the digital image for each of the metrics (A, B, C, X, Y, and W). The pixel coordinates (x and y coordinates) for the end points of each drawn line are recorded. A line is drawn on the calibration ruler between two marks that are 50 mm apart. The pixel coordinates for this line are recorded. The pixel coordinates for endpoints of each metric and the calibration ruler are entered into an appropriate computer spreadsheet program (e.g., Microsoft® Excel®). The spreadsheet may be programmed to computer the distance between endpoints, as measured in pixels, according to the following equation:

$$d = \sqrt{(x_1^2 - x_2^2) + (y_1^2 - y_2^2)}$$

where d=distance between two points $(x_1, y_1)$ and $(x_2, y_2)$. The distance in pixels for the calibration ruler, which is known to be 50 mm, can be use to convert the distance in pixels of any of the metric measurements into a distance in millimeters. The spreadsheet is programmed to convert length values based on pixel coordinates in millimeters.

The procedural steps are performed for the five duplicate samples. The distance values for each metric are averaged and the average is recorded.

EXAMPLES

Example 1 is a suitable example of the present invention. The chassis of this present example is constructed according to the description provided for a containment assembly in U.S. Pat. No. 5,151,092. The example has two back ears joined along the opposing rear longitudinal edges of the chassis. The back ears comprise a trilaminate with two outmost layers being a nonwoven available from BBA Nonwovens, Inc., Old Hickory, Tenn. as code HEC FPN 332D. Disposed between the two nonwoven layers is an elastic film available from Nordenia USA, Inc, Jackson, Mo. as code KG6361.100. A portion of the back ear is incrementally stretched according to the zero strain activation processes disclosed in U.S. Pat. Nos. 5,167,897 and 5,156,793, The back ear further comprises an engaging member which is a polymer film tab with a hook-bearing surface. The hook-bearing surface has an approximate area of 3.8 cm$^2$. The tab extends from the outboard edge of the back ear opposite the back ear edge that is joined to the chassis. The example further comprises a rectilinear receiving member disposed in the front waist region and on the garment facing surface of the chassis. The receiving member is a polymer film patch with fibrous loops on the garment-facing surface of the patch. The patch is available from Aplix Fasteners, Inc., Suffolk, UK as code AN29R95327873. The patch measures approximately 13.5 cm×5.0 cm with the long dimension running approximately parallel to the lateral edge of the chassis.

Example 2 is a commercially available comparative sample. The example is Pampers Cruisers size 4 diaper available from The Procter & Gamble Company, Cincinnati, Ohio.

Example 3 is a commercially available comparative sample. The example is Huggies® Supreme® size 4 available from the Kimberly-Clark Corp., Neenah, Wis.

Example 4 is a commercially available comparative sample. The example is Baby-Shaped®Huggies® size 4 available from the Kimberly-Clark Corp., Neenah, Wis.

Test Results

|  | A | B | C | A + C | X | Y |
|---|---|---|---|---|---|---|
| Example 1 | 0 (0) | 45.2 (5.7) | 5.7 (0.7) | 5.7 | 32.5 (1.5) | 33.8 (1.1) |
| Example 2 | 8.7 (2.8) | 64.1 (7.7) | 15.9 (1.4) | 24.6 | 47.1 (2.4) | 46.3 (1.7) |
| Example 3 | 5.2 (5.0) | 49.0 (3.2) | 17.8 (3.5) | 23.0 | 40.4 (4.9) | 43.8 (3.5) |
| Example 4 | 4.8 (2.6) | 29.2 (2.1) | 12.8 (2.5) | 17.6 | 44.1 (1.3) | 47.4 (1.6) |

All measurements in millimeters. Standard deviation presented in parenthesis.

|  | C/B | (A + C)/B | (A + C)/X |
|---|---|---|---|
| Example 1 | 0.13 | 0.13 | 0.18 |
| Example 2 | 0.25 | 0.38 | 0.52 |
| Example 3 | 0.36 | 0.47 | 0.57 |
| Example 4 | 0.44 | 0.60 | 0.40 |

Figure 6:
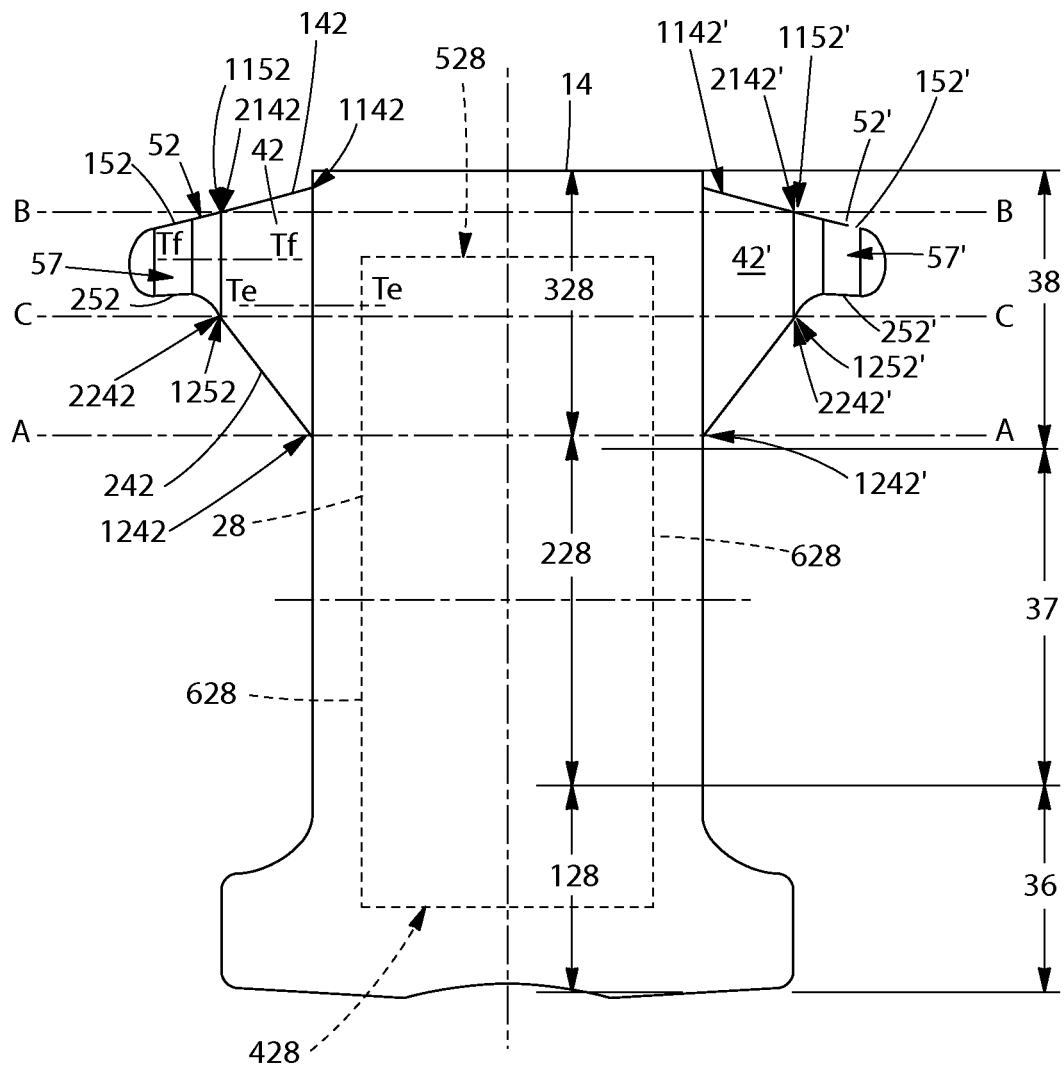
FIG. 6 is a schematic body facing surface view of an absorbent article according to one embodiment of the invention.
Figure 7:
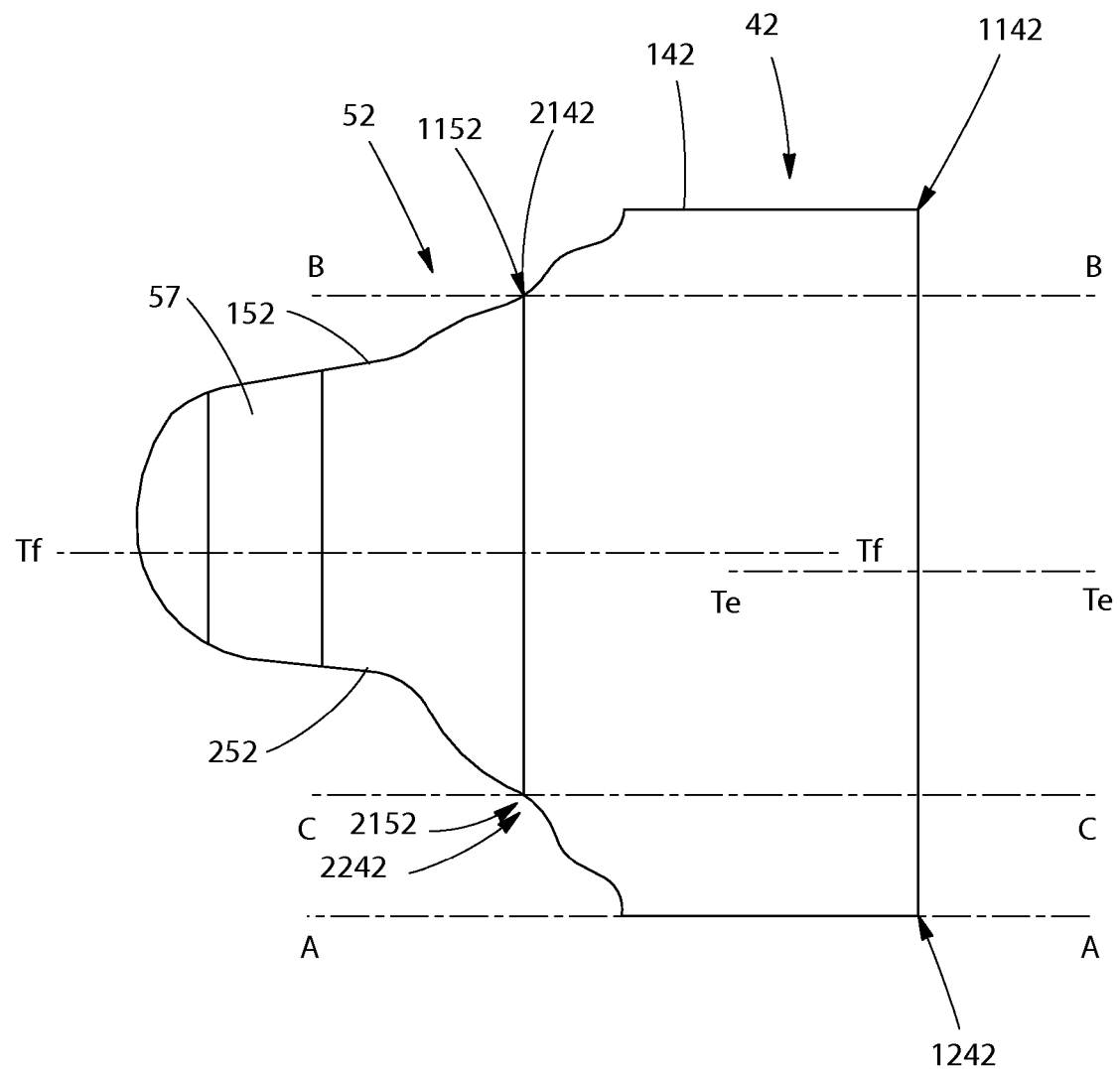
FIG. 7 depicts an elastically elongatable ear and a fastening tab.

In one embodiment schematically represented in FIG. 6, an absorbent article includes an absorbent core 28 that extends longitudinally between the front waist region 36 and the rear waist region 38, which is disposed in a front section 128, a middle section 228 and a back section 328 of the absorbent article. The absorbent core includes a front edge 428, a back edge 528 and side edges 628. The front section 128 is the section of the absorbent article that is generally disposed in the front waist region 36 of the chassis. The back section 328 is the section of the absorbent article that is disposed between the lateral back edge of the chassis and the transverse line A-A connecting the proximal ends of the lower edge of each of the left and right back ears 42. It should be noted that the back section 328 does not necessarily coincide with the rear waist region 38 of the article. The middle section 228 is the section of the absorbent article that is generally disposed between and interconnects the front section 128 to the back section 328. In one embodiment, at least part of an absorbent core is disposed in at least one of the front section 128, the middle section 228 and the back section 328 of the absorbent article. In one embodiment, an absorbent core is disposed in the middle section 228 and extends into the at least part of the front section 128 and/or into the back section 328. In one embodiment, the part of the absorbent core that is disposed in the front, middle section, or the back section is substantially cellulose free. In one embodiment the back section 328 comprises an absorbent core that is substantially cellulose free. In one embodiment, at least one of the front section 128, the middle section 228 and the back section 328 of the absorbent article comprises an absorbent core and has an average caliper of less than 1.5 mm, less than 1.25 mm, less than 1 mm, less than 0.75 mm or even less than 0.5 nm. In one embodiment, the back section 328 of the absorbent article comprises an absorbent core and has an average caliper of less than 1.5 mm., less than 1.25 mm, less than 1 mm, less than 0.75 mm or even less than 0.5 mm. A suitable method to measure the average caliper of a section of an absorbent article is discussed below. Among other benefits, it is believed that an absorbent article having at least one of, or even all of its front, middle and back sections that are thin is much more flexible than a thicker absorbent article while still maintaining its ability to absorb and retain body exudates. A thin absorbent article can more easily conform to the wearer's body shape and consequently, is more underwear-like. In addition, a thin absorbent article provides a snug fit around the waist and legs of a wearer. An absorbent article having a thin back section also allows tensions (caused by the forces created by elastically stretchable ears or side panels when the article is attached to the wearer) that are applied transversely on the article backsheet to be closer to the wearer's skin. Tensions that are applied in close proximity to the wearer's skin can prevent the article from "sliding" down the wearer's lower back and buttocks, especially after one or more discharges of body exudates. But it is also believed that when the front and/or back sections of the article are thin, these sections may have a tendency to fold-over when a longitudinal side of these sections is subjected to lateral forces. It is observed, for instance, that when a caregiver pulls on a tape tab (such as the one represented in FIG. 1A) for extending the back ear of the article, at least a portion of the back section of the article may fold-over inward or outward. The folding-over of the back section may cause discomfort to the wearer. Moreover, it may result in an inefficient use of the absorbent core positioned in the portion that is folded-over and it may also cause leakage or exudates run-off if a portion of the back section is folded outward. Without intending to be bound by any theory, it is believed that this folding-over of the back section occurs when the outermost line of tension (resulting from an elongation of the back ear) is located away from the lateral back edge of the chassis. It is also believed that the distance between the outermost and innermost lines of tension affects the folding-over of the back section. One of ordinary skill will appreciate that a relatively short distance between the outermost and innermost lines of tension result in a concentration of forces over a relatively narrow area whereas a longer distance between the outermost and innermost lines of tension result in a better distribution of the forces over a larger area. It is also believed that an "abrupt" change in thickness (in the longitudinal direction) from the portion of the back section that includes the absorbent core to the portion of the back section that does not include the absorbent core may create a weakness or path of least resistance which is followed by the lines of tension and causes the back section to fold over. In order to minimize or possibly eliminate this folding-over, one embodiment of an absorbent article includes a pair of fastening tabs (i.e. an engaging member) 52 and 52' that are each connected to an elastically elongatable ear 42 (respectively 42'). It will be understood that the fastening tab 52 is the element of the fastening system that includes a fastener 57 and is generally stiffer and less extensible than the elongatable ear. A fastening tab may be a separate web of material joined to the ear such as a tape tab as represented in FIG. 1A. The fastener 57 may be at least one of a plurality of hooks protruding away from the fastening tab, loops, an adhesive, a cohesive, or any other fastening member suitable to attach the article about the lower torso of a wearer. A fastening tab can also be integrally formed with the ear as shown in FIG. 6. For the sake of clarity and brevity, the description of the left fastening tab and back ear that follows is applicable to the right fastening tab and back ear and identical elements are referenced in the drawings with the same number with the prime symbol (for example, 52 and 52'). The left back ear 42 is a mirror image of the right back ear 42' and the left fastening tab 52 is a mirror image of the right fastening tab 52' relative to the absorbent article longitudinal axis. The fastening tab 52 represented in FIG. 6 includes an upper edge 152 with an upper proximal end 1152 and a lower edge 252 with a lower proximal end 1252. An elastically elongatable ear 42 includes an upper edge 142 with upper proximal and distal ends 1142, 2142 and a lower edge 242 with lower proximal and distal ends 1242, 2242. In one embodiment, the distance between the upper and lower proximal ends 1152, 1252 of a fastening tab 52 is at least 20 mm, at least 30 mm or even at least 40 mm. In one embodiment, the distance between the upper and lower proximal ends 1152, 1252 of a fastening tab 52 is between 20 mm and 80 mm, between 30 mm and 70 mm or even between 40 mm and 60 mm. In one embodiment, the back ears 42 and 42' are connected to the chassis such that the transversal line (represented in FIG. 6 by line BB) that includes the upper end 1152 of the left fastening tab 52 and the upper end 1152' of the right fastening tab 52' is positioned between the back lateral edge 14 of the chassis and the back edge 528 of the absorbent core. In one embodiment, the longitudinal distance between the transversal line (B. B) previously described and the back edge 14 of the chassis is less than 25 mm, less than 20 mm, less than 15 mm or even less than 10 mm. In one embodiment, the back ears 42, 42' are connected to the chassis such that the back edge 528 of the absorbent core is positioned between the transversal line B-B and the transversal line (represented in FIG. 6 by line CC) that includes the lower end 1252 of the left fastening tab 52 and the lower end 1252' of the right fastening tab 52'. In one embodiment, the distance between the upper distal end 2142 and the lower distal end 2242 of the elongatable back ear 42 is greater than the distance between the upper and lower proximal ends 1152, 1252 of a fastening tab 52. In one embodiment, the distance between the upper and lower distal ends 2142, 2242 of the elongatable back ear 42 is the same as the distance between the upper and lower proximal ends 1152, 1252 of a fastening tab 52. Among other benefits, it is believed that when the distance between the upper and lower distal ends 2142, 2242 of the elongatable back ear 42 is the same as the distance between the upper and lower proximal ends 1152, 1252 of a fastening tab 52, the lateral forces that are applied on the fastening tab 52 are better distributed across the ear 42 and maximizes usage of the ear material. In one embodiment, the distance between the upper and lower proximal ends 1142, 1242 of the back ear 42 is the same as the distance between the upper and lower distal ends 2142, 2242 of the back ear 42. In one embodiment illustrated in FIG. 6, the distance between the upper and lower proximal ends 1142, 1242 is greater than the distance between the upper and lower distal ends 2142, 2242. Among other benefits, it is believed that ears that are cut and sized such that the distance between the upper and lower proximal ends 1142, 1242 is greater than the distance between the upper and lower distal ends 2142, 2242 provide a more sustained fit around the wearer's legs and hips. In one embodiment, the distance between the upper and lower proximal ends 1142, 1242 of the back ear 42 is at least 5%, at least 10% at least 25% or even at least 50% greater than the distance between the upper and lower distal ends 2142, 2242 of the back ear 42. In one embodiment, the upper edge 152 of the fastening tab 52 is asymmetric to the lower edge 252 of the fastening tab relative to the transverse axis Tf of the fastening tab 52. The transverse axis Tf of the fastening tab 52 is the line that is equidistant from the upper and lower proximal ends 1152, 1252 of the fastening tab and is perpendicular to the line that includes the upper and lower proximal ends 1152, 1252 of the fastening tab. In one embodiment, the upper edge 142 of the elongatable back ear 42 is asymmetric to the lower edge 242 of the elongatable back ear relative to the transverse axis Te of the elongatable back ear. The transverse axis Te of the elongatable back ear 42 is the line that is equidistant from the upper and lower proximal ends 1142, 1242 of the back ear and is perpendicular to the line that includes the upper and lower proximal ends 1142, 1242 of the back ear 42. In one embodiment, the transverse axis Tf of the fastening tab 52 overlaps substantially with the transverse axis Te of the elongatable ear 42. In one embodiment, the transverse axis Tf of the fastening tab 52 is offset relative to the transverse axis Te of the elongatable ear 42. The transverse axis Tf of the fastening tab 52 and the transverse axis Te of the elongatable ear 42 can be separated by a distance of at least 5 mm, at least 10 mm, at least 15 ram or even at least 20 mm. In one embodiment, the back ears 42, 42' are connected to the chassis such that the lateral back edge 528 of the absorbent core 28 is positioned between the lateral back edge 14 of the chassis and the transverse axis Te of an elongatable back ear 42. In one embodiment, the back ears 42 and 42' are connected to the chassis such that the longitudinal distance between the transverse axis Te of the elongatable back ear 42 and the back edge 528 of the absorbent core is less than 50 mm, less than 40 mm, less than 30 mm or even less than 20 mm. In one embodiment, the longitudinal distance between the transverse axis Te of the elongatable back ear 42 and the back edge 528 of the absorbent core is between 0 mm and 50 mm, between 5 mm and 40 mm or even between 10 mm and 30 mm. In one embodiment, the back ears 42, 42' are connected to the chassis such that the transverse Tf axis of a fastening tab 52 is positioned between the back edge 14 of the chassis and the back edge 528 of the absorbent core 28. In one embodiment, the back ears 42, 42' are connected to the chassis such that the longitudinal distance between the transverse axis Tf of the fastening tab and the back edge 528 of the absorbent core is less than 50 mm, less than 40 mm, less than 30 mm or even less than 15 mm. In one embodiment, the longitudinal distance between the transverse axis Tf of the fastening tab 52 and the back edge 528 of the absorbent core is between 0 mm and 30 mm, between 2 mm and 20 mm or even between 2 mm and 15 mm. A magnified view of an elongatable ear 42 and fastening tab 52 is represented in FIG. 7 for clarity and also to illustrate that the ear 42 and fastening tab 52 may have a shape other than the shape represented in FIG. 6.

In one embodiment, the portion of the back section 328 of the chassis that is positioned between the back lateral edge 14 of the chassis and the back edge 528 of the absorbent core has an average caliper of less than 1 mm, less than 0.75 mm, less than 0.5 mm, or even less than 0.25 mm. In one embodiment, the longitudinal distance between the lateral back edge 14 of the chassis and the back edge 528 of the absorbent core is less than 100 mm, less than 90 mm or even less than 80 mm. In one embodiment, the longitudinal distance between the back lateral edge 14 of the chassis and the back edge 528 of the absorbent core is at least 10 mm, at least 15 mm or even at least 20 mm. In one embodiment, the back section of the absorbent article has an Average Caliper Differential of less than 1.25 mm, less than 1 mm, less than 0.75 mm or even less than 0.5 mm. In one embodiment, the back section of the absorbent article has an Average Caliper Differential of between 0.1 mm and 1.25 mm, between 0.1 mm and 1 mm, between 0.1 mm and 0.5 mm or even between 0.1 mm and 0.25 mm. The Average Caliper Differential of a section of the an absorbent article can be determined by measuring the average caliper of the portion of the back section of the chassis positioned between the back lateral edge of the chassis and the back edge of the absorbent core and the average caliper of the back section of the chassis that comprises an absorbent core. The average caliper of the portion of the back section of the chassis positioned between the back lateral edge of the chassis and the back edge of the absorbent core is then deducted from the average caliper of the back section of the chassis that comprises an absorbent core. Without intending to be bound by any theory, it is believed that a back section of an absorbent article having such an Average Caliper Differential is less likely to fold-over along the edge of the absorbent core.

Caliper Test
 Equipment:
  Caliper Instrument One Sokki digital caliper gauge DG-3610 connected to an Ono Sokki linear gauge sensor GS-503

Contact Foot: Flat circular foot with a diameter of 40 mm (+/− (15 mm)
  Weigh/Pressure: Total weight of foot and shaft equals 80+/−2 g to equal approximately 0.1 PSI applied to the sample. A circular weight may be applied to the foot (i.e., a weight with a slot to facilitate application around the shaft) to achieve the target weight.
  Ruler—Calibrated metal ruler graduated in mm.
  Stopwatch—Accuracy 1 second
  Sample Preparation:
   1. If the absorbent articles are in their original, unopened package, the sample articles to be tested are removed from the center area of the package. If the package contains more than 4 products, the outer most two articles on each side of the package are not used in the testing.
   2. If the absorbent article has been out of its original package for more than 15 minutes, place it under an even pressure of 0.345 N/cm2 ((0.5 lb/in2) for 30 minutes.
   3. Physical manipulation of product should be minimal and restricted only to necessary sample preparation.
   4. As the diapers relax (i.e. expand) when removed from the compressed condition, the time between removal from the package and the actual caliper testing may be impact the measurement, Consequently, caliper readings should be taken approximately 5 to 15 minutes after the product is removed from the package or from under the applied pressure (as previously described).
   5. Cut or remove any elastic components of the article that prevent the article from being laid flat under the caliper foot. These may include leg cuffs or waistbands. Avoid touching absorbent core area and do not compress the absorbent core area with the hands
   6. Mark the measuring point(s) gently on the diaper with a permanent felt tip marker.
  Caliper Measurement Location:
   a) Lay article flat on a counter top,
   b) Measure the uncontracted length of the article between the front and back edges along the longitudinal axis of the article. Record this measurement.
   c) Divide the length by eight.
   d) Very gently mark a lateral measurement line across the back portion of the article at a distance of one-eight the article length from the back waist edge of the article, using a permanent felt tip marker.
   e) Very gently mark a line along the longitudinal axis of the article in the back portion of the article using a permanent felt tip marker.
   f) At a distance of 20 mm laterally outboard of each side of the line indicating the longitudinal axis, very gently mark a 40 mm longitudinal measurement line parallel with the longitudinal axis and bisected by the lateral measurement line.
   g) The intersections of the lateral measurement line and the two longitudinal measurement lines represent the locations where the center of the caliper foot will contact during the caliper measurement. These intersections are referred to as the "marked measuring points".
  Caliper Measurement Steps:
   1. Raise the caliper gauge contact foot and place the article on the caliper gauge base plate, garment-facing surface side down.
   2. With the foot raised, position the article on the base plate in a manner that when lowered, the center of the foot is on one of the marked measuring points.
   3. Gently lower the foot onto the diaper
   4. Read the caliper value to the nearest 0.01 mm, 5 seconds after the foot comes in contact with the diaper, Record the caliper measurement.

5. Reset the instrument reading to zero after each measurement.

6. Repeat steps 1 through 5 for the second marked measuring point.

Caliper Calculations:

For each article, average the two caliper measurements to calculate the rear waist region caliper for that article. Generally, at least five samples are measured in this manner for a given product and the rear waist region calipers may be aggregated to calculate an average and standard deviation.

Absorbent Core.

Figure 8:
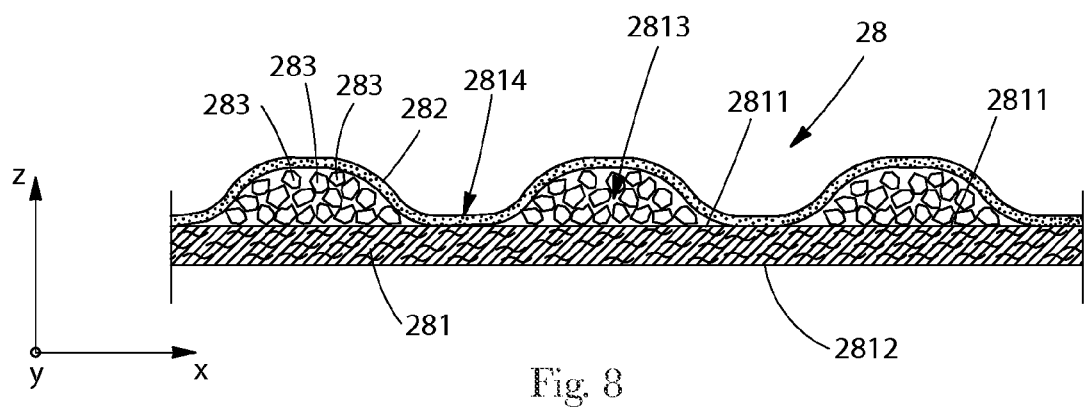
FIG. 8 is a schematic cross section view of an example of an absorbent core-suitable in one embodiment of the invention.
Figure 9:
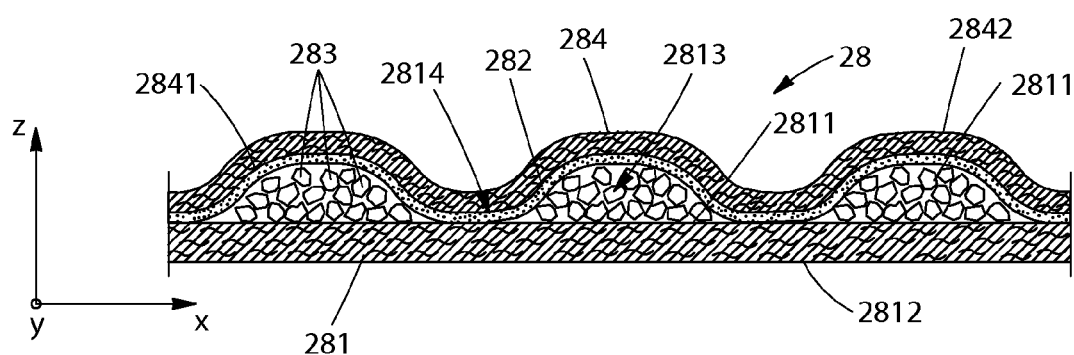
FIG. 9 is a schematic cross section view of another example of an absorbent core suitable in one embodiment of the invention.
Figure 10:
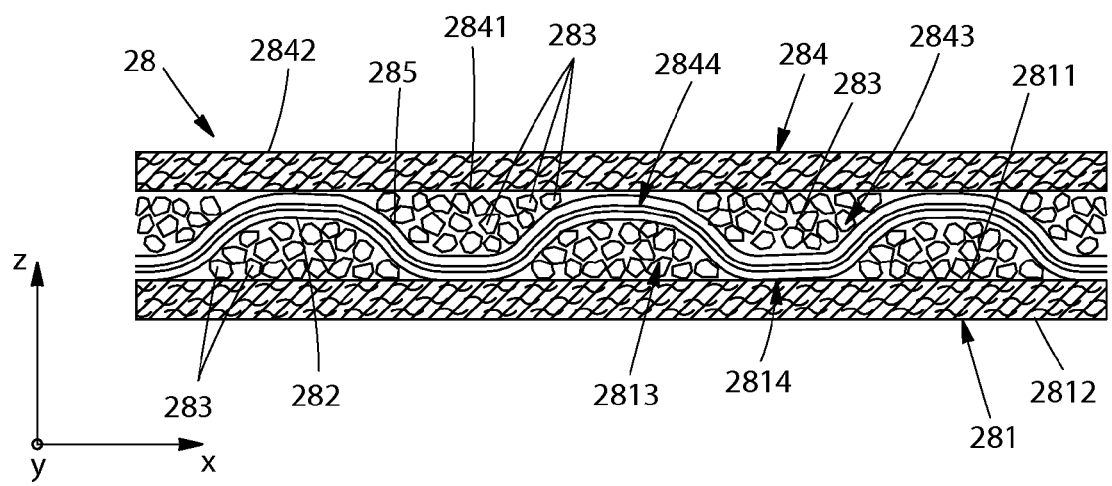
FIG. 10 is a schematic cross section view of another example of an absorbent core suitable in one embodiment of the invention.

In one embodiment, an absorbent article includes an absorbent core 28 that is substantially cellulose free. Cross-sectional views of examples of suitable absorbent cores are schematically represented in FIGS. 8-10. The absorbent core 28 is the element of the absorbent article whose primary function is to absorb and retain liquid body exudates. Additional elements may be added between the topsheet and the absorbent core of an absorbent article to facilitate the acquisition and the distribution of body exudates. Such elements may include, for example, an acquisition layer and/or a distribution layer as it is well known in the art. The acquisition and/or distribution layers may themselves be substantially cellulose free (for example made entirely of a nonwoven material) or include a significant amount of cellulosic material. Although an absorbent core generally includes absorbent materials in particulate form having a high retention capacity such as, for example absorbent polymers, these materials do not need to be present along the entire length of the absorbent core. It may be advantageous to provide an absorbent core with a greater amount of absorbent material in the crotch area and/or the front waist region in comparison to the back waist region which may include only a little amount, if any, of absorbent polymers. In one embodiment, an absorbent core 28 comprises first and second layers of material 281, 282 and an absorbent material 283 disposed between the first and second layers 281, 282. In one embodiment the first and second layers of material can be a fibrous material chosen from at least one of a nonwoven fibrous web, a woven fibrous web and a layer of thermoplastic adhesive material. Although the first and second layers can be made of a same material, in one embodiment, the first layer 281 is a nonwoven fibrous web and the second layer 282 is a layer of thermoplastic adhesive material. A nonwoven fibrous web 281 can include synthetic fibers, such as mono-constituent fibers of PE, PET and PP, multi-constituent fibers such as side by side, core/sheath or island in the sea type fibers. Such synthetic fibers may be formed via a spunbonding process or a meltblowing process. The nonwoven fibrous web 281 may include a single layer of fibers but it may also be advantageous to provide the nonwoven web with multiple layers of fibers such as multiple layers of spunbond fibers, multiple layers of meltblown fibers or combinations of individual layer(s) of spunbond and meltblow fibers. In one embodiment, the nonwoven web 281 can be treated with an agent (such as a surfactant) to increase the surface energy of the fibers of the web. Such an agent renders the nonwoven web more permeable to liquids such as urine. In another embodiment, the nonwoven web can be treated with an agent (such as a silicone) that lowers the surface energy of the fibers of the nonwoven web. Such an agent renders the nonwoven web less permeable to liquids such as urine.

The first layer 281 comprises a first surface 2811 and a second surface 2812 and at least regions 2813 of the first surface are in direct facial relationship with a significant amount of absorbent material 283. In one embodiment an absorbent material is deposited on the first surface 2811 in a pattern to form regions 2813 on the first layer 281, which are in direct facial relationship with a significant amount of absorbent polymer material 283 and regions 2814 on the first web that are in facial relationship with only an insignificant amount of absorbent material. By "direct facial relationship with a significant amount of absorbent material" it is meant that some absorbent material is deposited on top of the regions 2813 at a basis weight of at least 100 g/m$^2$, at least 250 g/m$^2$ or even at least 500 g/m$^2$. The pattern may include regions that all have the same shape and dimensions (i.e. projected surface area and/or height). In the alternative the pattern may include regions that have different shape or dimensions to form a gradient of regions. At least some of the regions 2813 can have a projected surface area of between 1 cm$^2$ and 150 cm$^2$ or even between 5 cm$^2$ and 100 cm$^2$. By "facial relationship with an insignificant amount of absorbent material" it is meant that some absorbent material may be deposited on top of the regions 2814 at a basis weight of less than 100 g/m$^2$, less than 50 g/m$^2$ or even substantially no absorbent material. At least some of the regions 2814 can have a projected surface area of between 1 cm$^2$ and 150 cm$^2$ or even between 5 cm$^2$ and 100 cm$^2$. The aggregate projected surface area of all the regions 2813 can represent between 10% and 90% or even between 25% and 75% of the total projected surface area of the first surface 2811 of the first layer 281. In one embodiment, the second layer 282 is a layer of a thermoplastic adhesive material. "Thermoplastic adhesive material" as used herein is understood to mean a polymer composition from which fibers are formed and applied to the absorbent material with the intent to immobilize the absorbent material in both the dry and wet state. Non-limiting examples of thermoplastic adhesive material may comprise a single thermoplastic polymer or a blend of thermoplastic polymers. The thermoplastic adhesive material may also be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>$Tg$<16°$ C. In certain embodiments, typical concentrations of the polymer in a hot melt are in the range of about 20 to about 40% by weight. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are polymers prepared using single-site or metallocene catalysts. In exemplary embodiments, the tackifying resin has typically a Mw below 5,000 and a Tg usually above room temperature, typical concentrations of the resin in a hot melt are in the range of about 30 to about 60% by weight, and the plasticizer has a low Mw of typically less than 1,000 and a Tg below room temperature, with a typical concentration of about 0 to about 15%.

The thermoplastic adhesive material 282 can be disposed substantially uniformly within the absorbent material 283. In the alternative and as represented in FIG. 8, the thermoplastic adhesive material 282 can be provided as a fibrous layer disposed on top of the absorbent material 283 and the regions 2814 of the first surface 2811 that are in facial relationship with only an insignificant amount of absorbent material. In one embodiment, a thermoplastic adhesive material is applied at an amount of between 1 and 20 g/m$^2$, between 1 and 15 μm$^2$ or even between 2 and 8 g/m$^2$. The discontinuous deposition of absorbent material on the first layer 281 imparts an essentially three-dimensional structure to the fibrous layer of thermoplastic material 282. In other words, the layer of thermoplastic adhesive material follows the topography resulting from the absorbent material 283 deposited on the first nonwoven fibrous web 281 and the regions 2814 that only include insignificant amounts of absorbent material. Without intending to be bound by any theory, it is believed that the thermoplastic adhesive materials disclosed herein enhance immobilization of the absorbent material in a dry and wet state.

In one embodiment, the absorbent core 28 may further comprise a second layer of a nonwoven fibrous material 284 as represented in FIG. 9. This second layer may be provided of the same material as the nonwoven fibrous layer 281, or in the alternative may be provided from a different material. It may be advantageous for the first and second nonwoven fibrous layers 281, 284 to be different in order to provide these layers with different functionalities. In one embodiment, the surface energy of the first nonwoven layer can be different than the surface energy of the second nonwoven layer. In one embodiment, the surface energy of the second nonwoven layer is greater than the surface energy of the first nonwoven layer. Among over benefits, it is believed that when the surface energy of the second nonwoven layer is greater than the surface energy of the first nonwoven layer, liquids such as urine will be able to penetrate the second nonwoven layer more easily in order to reach and be retained by the absorbent material while at the same time reducing the chances that the liquid may penetrate and go through the first layer. This may be particularly advantageous when the first nonwoven layer is disposed against the backsheet of an absorbent article. The different surface energies of each layer may be obtained, for example, by applying a different amount of an agent such as a surfactant to the second nonwoven layer than the amount of surfactant (if any) applied to the first nonwoven layer. This may also be achieved by applying a different type of surfactant to the second nonwoven layer than the surfactant applied to the first nonwoven layer. This may still be achieved by applying a material to the first nonwoven layer that lowers its surface energy. In addition to having different surface energies, or in the alternative, the first and second nonwoven fibrous layers 281, 284 may also be different structurally. In one embodiment, the first nonwoven layer 281 may include different layers of fibers than the second nonwoven layer. For example, the second nonwoven layer 284 may only include one or more layers of spunbond fibers whereas the first nonwoven layer 281 includes one or more layers of spundbond fibers and one or more layers of meltblown fibers. In another embodiment, both nonwoven fibrous layers 281, 284 may include one or more layers of spunbond fibers and one or more layers of meltblow fibers but the first and second layers 281, 284 differ in terms of at least one of the chemical composition of the fibers used to form the nonwoven material, the denier of the fibers and/or the basis weight of the nonwoven material. In addition to or in the alternative than the above the first and second nonwoven layers 281, 284 may also differ in terms of at least one of their respective hydrohead values, their respective porosity, their respective Frazier permeability and their respective tensile properties. The second nonwoven layer 284 may applied directly on top of the first nonwoven layer 281, the absorbent material 283 and the thermoplastic adhesive material 282. As a result, the first and second nonwoven layers 281 and 284 further encapsulate and immobilize the absorbent material 283.

The regions 2813 may have any suitable shape in the x-y dimension (i.e. the horizontal plane) of the absorbent core. In one embodiment, the regions 2813 form a pattern of disc that are spread on the first surface of the first web 281. In one embodiment, the regions 2813 form a pattern of longitudinal "strips" or "bars" that extend continuously along the longitudinal axis of the absorbent core (i.e. along the y dimension) and are spread apart from each other. In one embodiment, the regions 2813 form a pattern of longitudinal "strips" or "bars" that extend continuously along the transverse axis of the absorbent core (i.e. along the x dimension). In an alternative embodiment, these strips may be are arranged to form an angle of at between 1.0 and 90 degrees, between 20 and 80 degrees, between 30 and 60 degrees, or even 45 degrees relative to the longitudinal axis of the absorbent article. In one embodiment, a "strip" or "bar" can have a substantially rectangular shape with the longest side of the rectangle being at least twice, 5 times, even 25 times, or even 50 times as long as the shortest side of the rectangle formed by the "strip" or "bar."

In one embodiment schematically represented in FIG. 10, the second nonwoven layer 284 has a first surface 2841 and a second surface 2842 and an absorbent material 283 applied to its first surface 2841 in order to form a pattern of regions 2843 that are in direct facial relationship with a significant amount of absorbent material 283 and regions 2844 on the first surface 2841 that are in facial relationship with only an insignificant amount of absorbent material as previously discussed. In one embodiment, a thermoplastic adhesive material 285 may further be applied on top of the second nonwoven layer 284 as previously discussed in the context of the first web/absorbent material/thermoplastic adhesive material composite. The second nonwoven layer 284 may then be applied on top of the first nonwoven layer 281. In one embodiment, the pattern of absorbent material present on the second nonwoven layer 284 may be the same as the pattern of absorbent material present on the first nonwoven layer 281. In an other embodiment, the patterns of absorbent material that are present on the first and second nonwoven layers are different in terms of at least one of the shape of the regions, the projected surface areas of the regions, the amount of absorbent material present on the regions and the type of absorbent material present on the regions. It is believed that when the patterns of absorbent material that are present on the first and second nonwoven layers are different, each layer/absorbent composite may have different functionalities such as for example, different absorbent capacities and/or different acquisition rates of liquids. It can be beneficial for example to provide an absorbent core with a structure where the second pattern formed by the regions 2843 of absorbent material (i.e. on the second nonwoven layer 284) exhibits a slower acquisition rate than the first pattern of regions 2813 of absorbent material in order to allow liquids, such as urine, to reach and be absorbed by the absorbent material deposited on the first nonwoven layer 281 before expansion of the absorbent material in the regions 2843. Such a structure avoids any significant gel blocking by the absorbent material present in the regions 2843. It can also be advantageous to apply the second layer/absorbent material/thermoplastic adhesive material composite in such a way that at least some of or even all of the regions 2813 of the first nonwoven layer 281 that are in direct facial relationship with a significant amount of absorbent material are also in substantial facial relationship with corresponding regions 2844 of the second web 284, which are in facial relationship with an insignificant amount of absorbent material.

The absorbent core 28 may also comprise an auxiliary adhesive which is not illustrated in the figures. The auxiliary adhesive may be deposited on at least one of or even both the first and second nonwoven layers 281, 284 before application of the absorbent material 283 in order to enhance adhesion of the absorbent material as well as adhesion of the thermoplastic adhesive material 282, 285 to the respective nonwoven layers 281, 284. The auxiliary adhesive may also aid in immobilizing the absorbent material and may comprise the same thermoplastic adhesive material as described hereinabove or may also comprise other adhesives including but not limited to sprayahle hot melt adhesives, such as RB. Fuller Co. (St. Paul, Minn.) Product No. HL-1620-B. The auxiliary adhesive may be applied to the nonwoven layers 281, 284 by any suitable means, but according to certain embodiments, may be applied in about 0.5 to about 1 mm wide slots spaced about 0.5 to about 2 mm apart. Non-limiting examples of suitable absorbent material 283 include absorbent polymer material such as cross linked polymeric materials that can absorb at least 5 times their weight of an aqueous 0.9% saline solution as measured using the Centrifuge Retention Capacity test (Edana 441.2-01). In one embodiment, the absorbent material 283 is absorbent polymer material which is in particulate form so as to be flowable in the dry state.

As previously discussed, the absorbent material 283 present in the absorbent cores 28 of an absorbent article and more particularly illustrated in FIGS. 8-10, does not need to be present along the entire length of the absorbent core. In one embodiment, the back section 328 of an absorbent article includes an insignificant amount of absorbent material 283 whereas at least the middle 228 and/or the front section 128 include a greater amount of absorbent material than the back section 328. For example, the back section 328 may include less than 5 grams, or less than 3 grams, less than 2 grams or even less than 1 g of a particulate absorbent polymer material. The middle section 228 may include at least 5 grams, or at least 8 grams, or even at least 10 grams of a particulate absorbent polymer material. The front section 128 may include between 1 and 10 grams, or between 2 and 8 grams of a particulate absorbent polymer material.

In addition, it should be noted that the front and back edges of the absorbent chassis of the article are shown as being linear in FIGS. 1A through 3B. However, either the back and/or the front edges may have a shape other than linear, Suitable non-linear shapes are disclosed in U.S. Pat. No. 7,361,167 issued on Apr. 22, 2008, to Erickson et al. and assigned to The Procter and Gamble Company.

Figure 11:
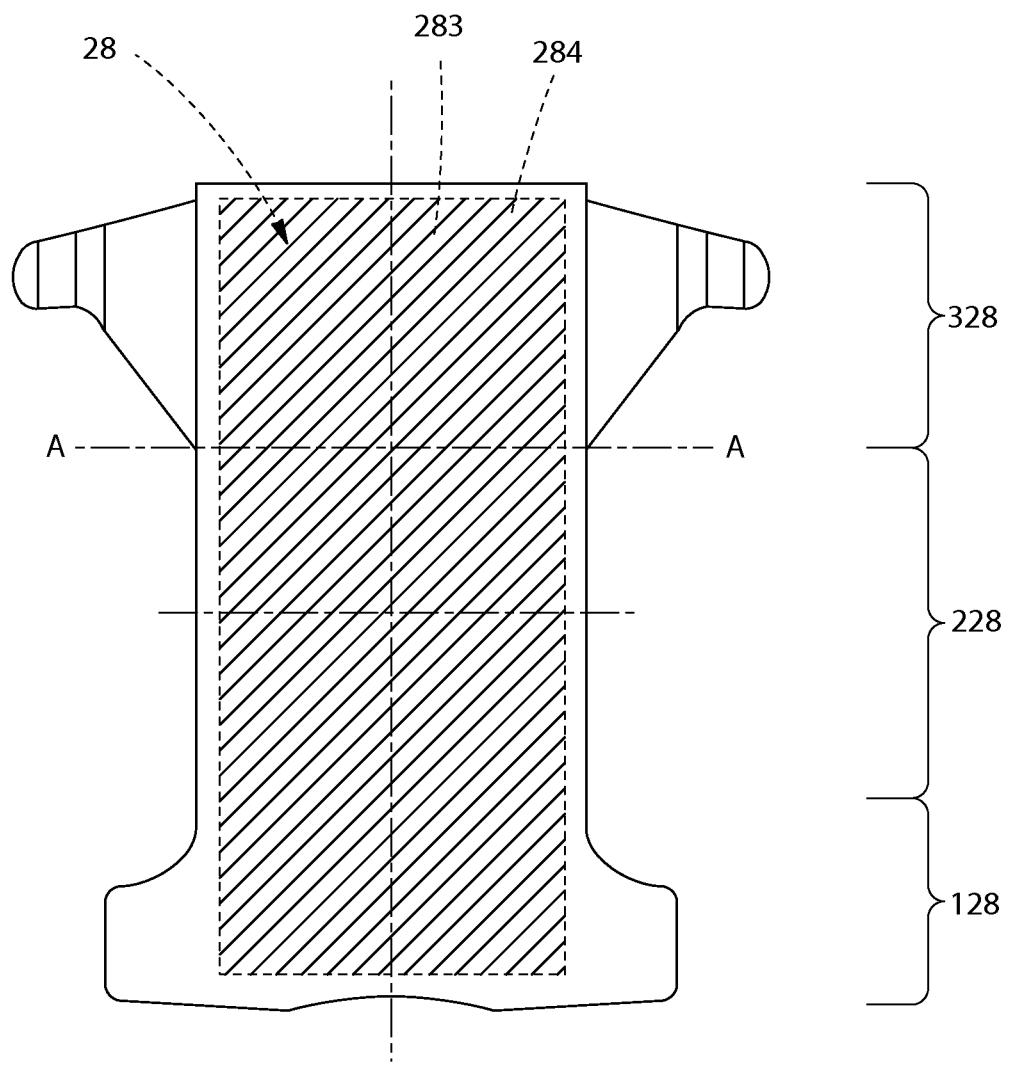
FIG. 11 is a schematic body facing surface view of an absorbent article with an absorbent core according to one embodiment of the invention.
Figure 12:
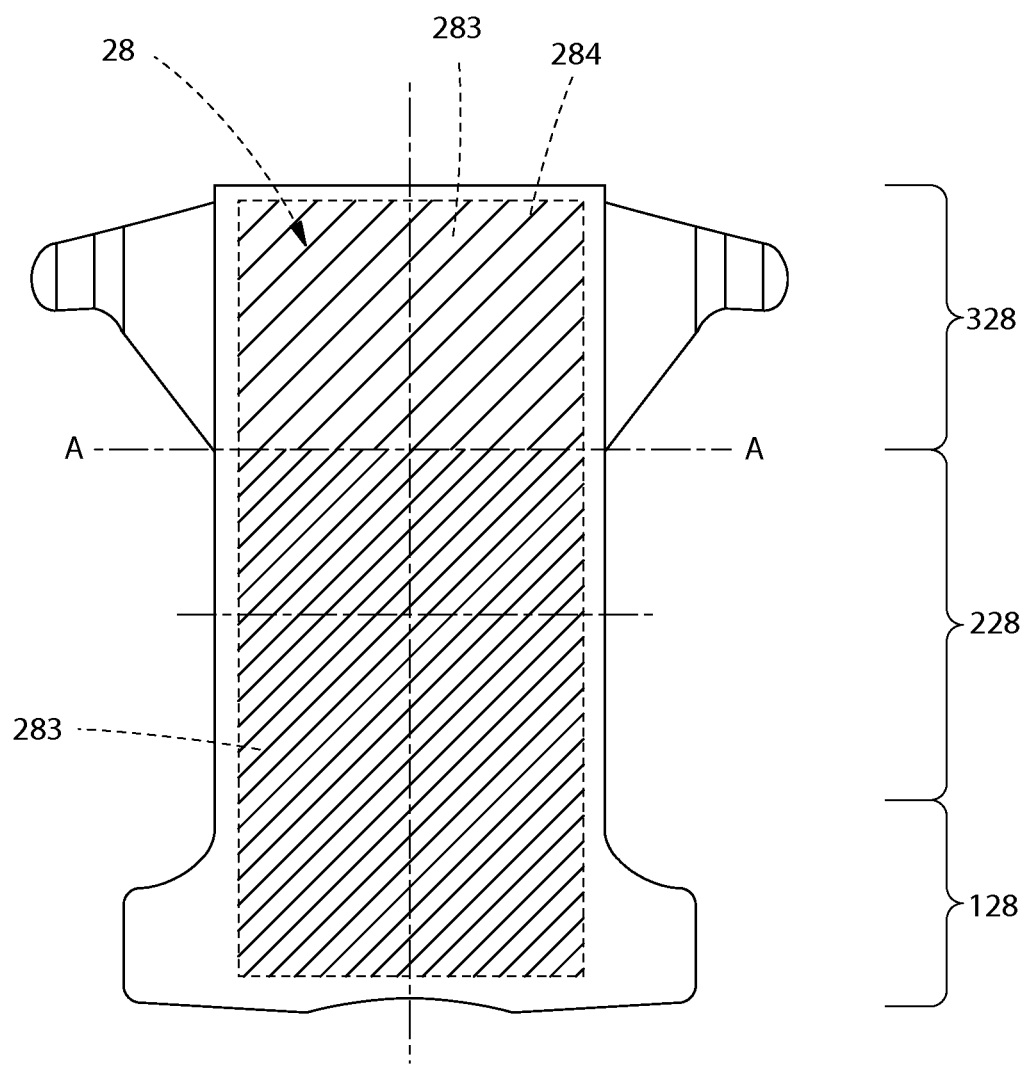
FIG. 12 is a schematic body facing surface view of an absorbent article with an absorbent core according to another embodiment of the invention.
Figure 13:
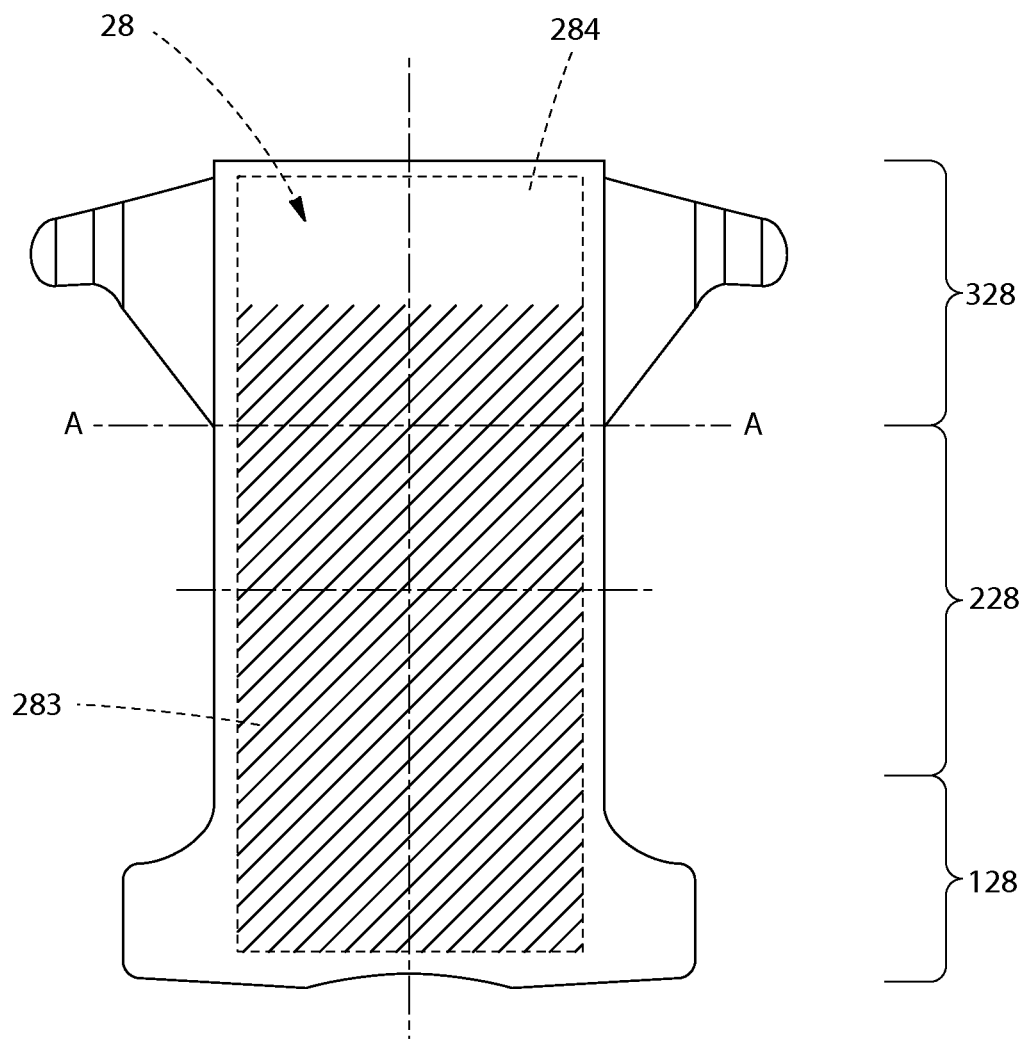
FIG. 13 is a schematic body facing surface view of an absorbent article with an absorbent core according to another embodiment of the invention.
Figure 14:
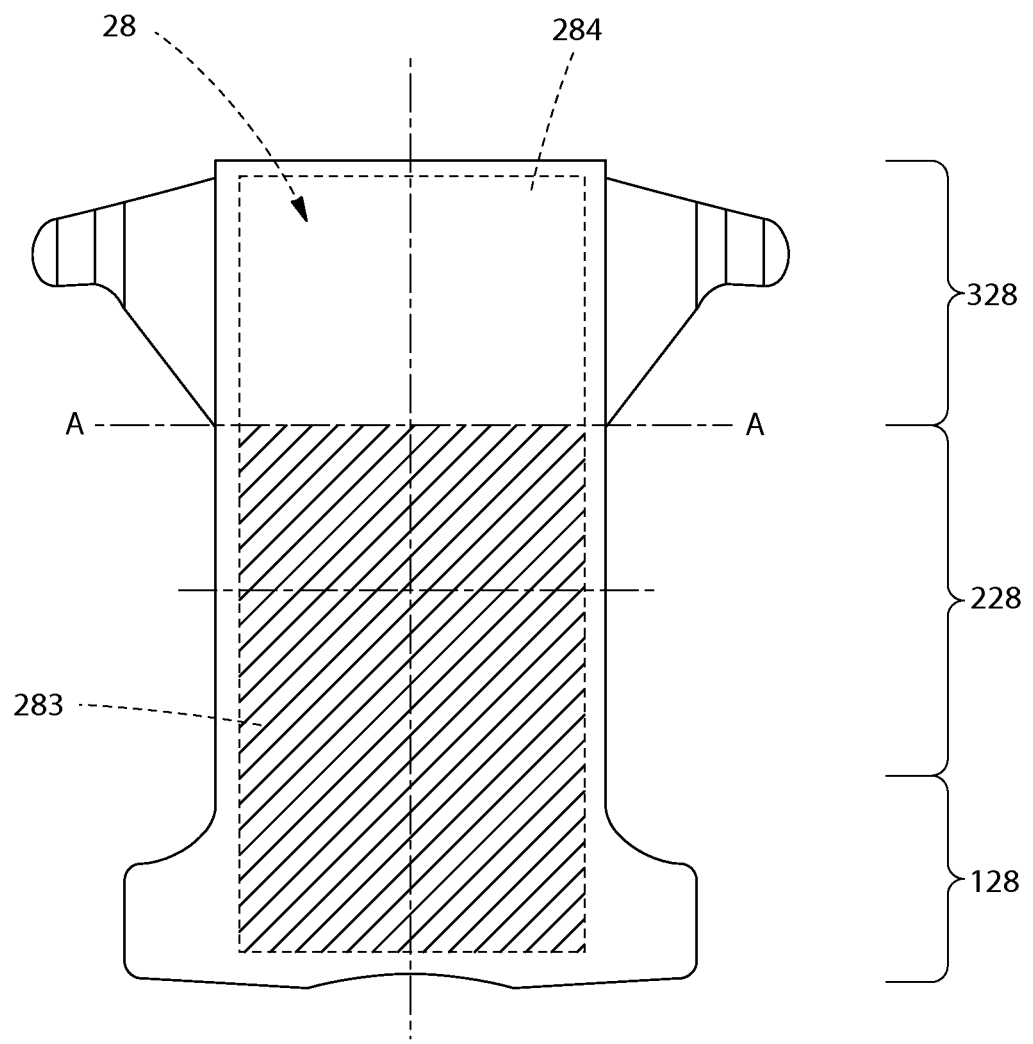
FIG. 14 is a schematic body facing surface view of an absorbent article with an absorbent core according to another embodiment of the invention.
Figure 15:
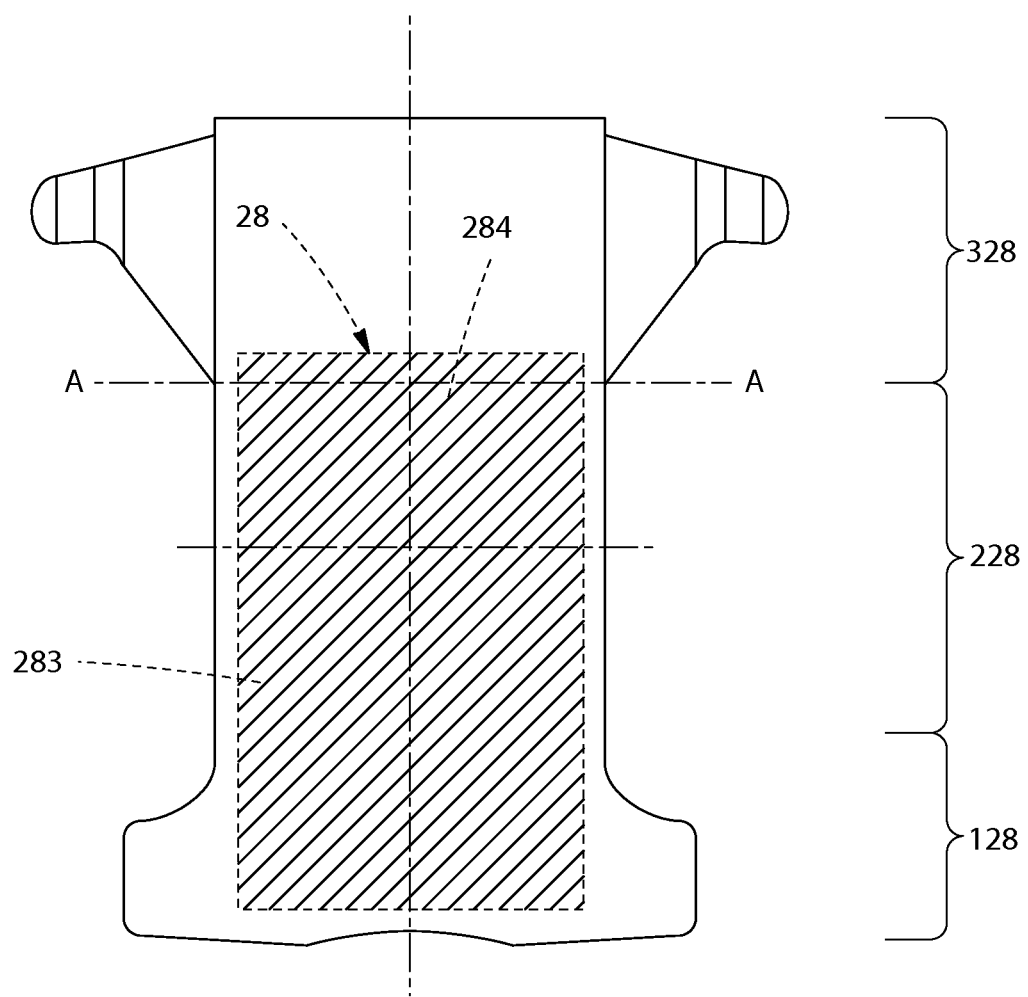
FIG. 15 is a schematic body facing surface view of an absorbent article with an absorbent core according to another embodiment of the invention.
Figure 16:
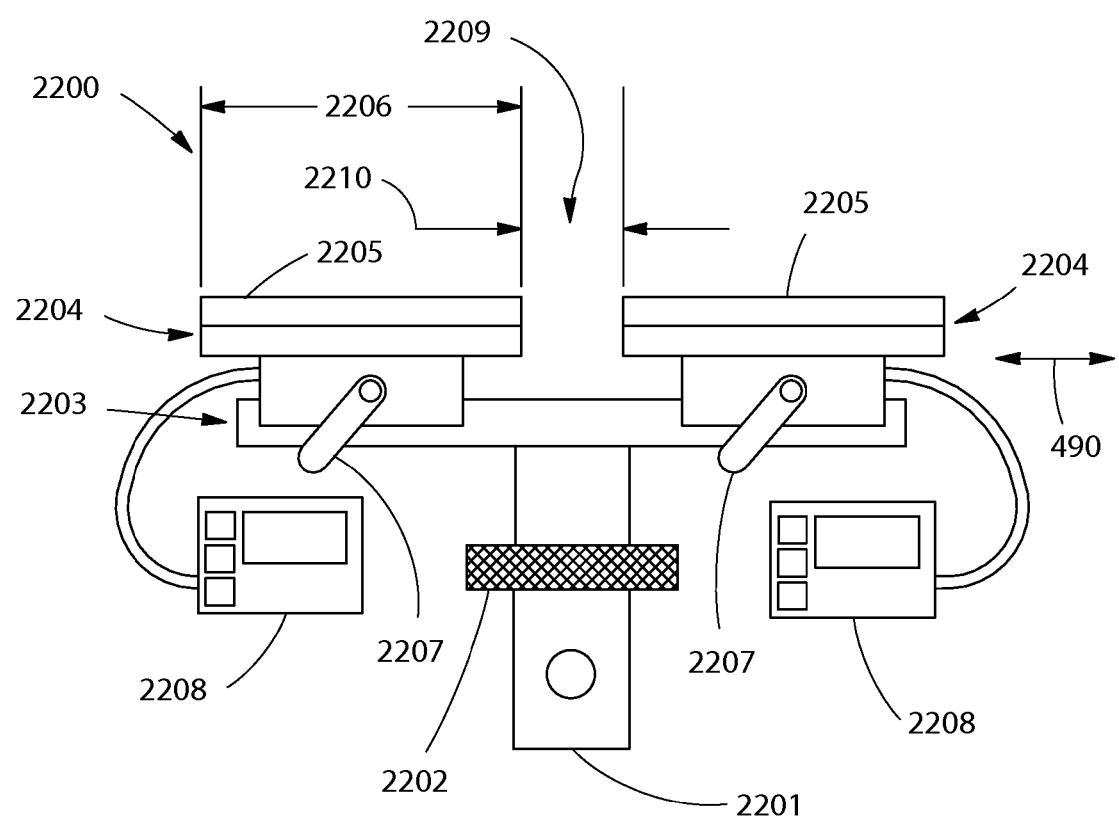
FIG. 16 is an elevation view showing an apparatus for testing the bending stiffness of materials.
Figure 17:
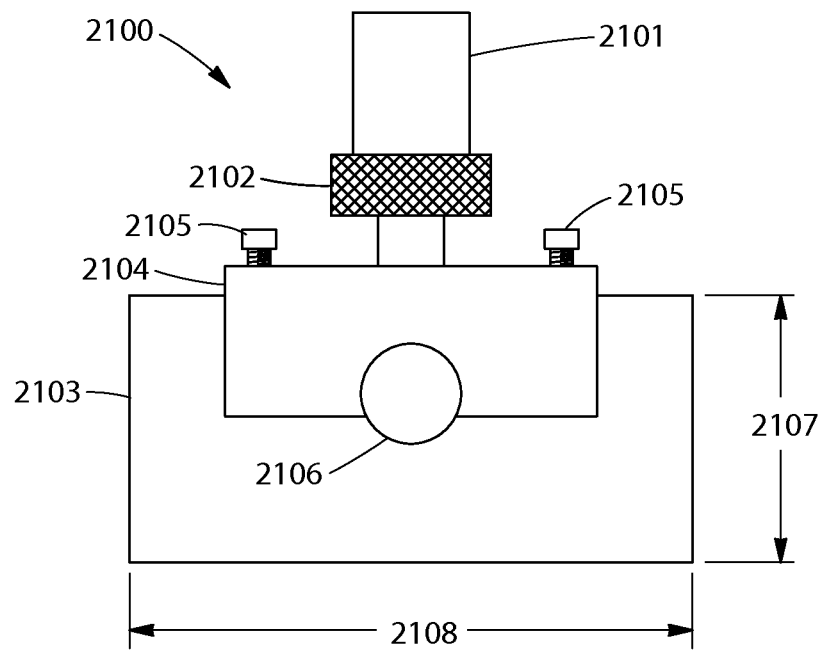
FIG. 17 is a front elevation view showing a plunger for use with the apparatus of FIG. 16.
Figure 18:
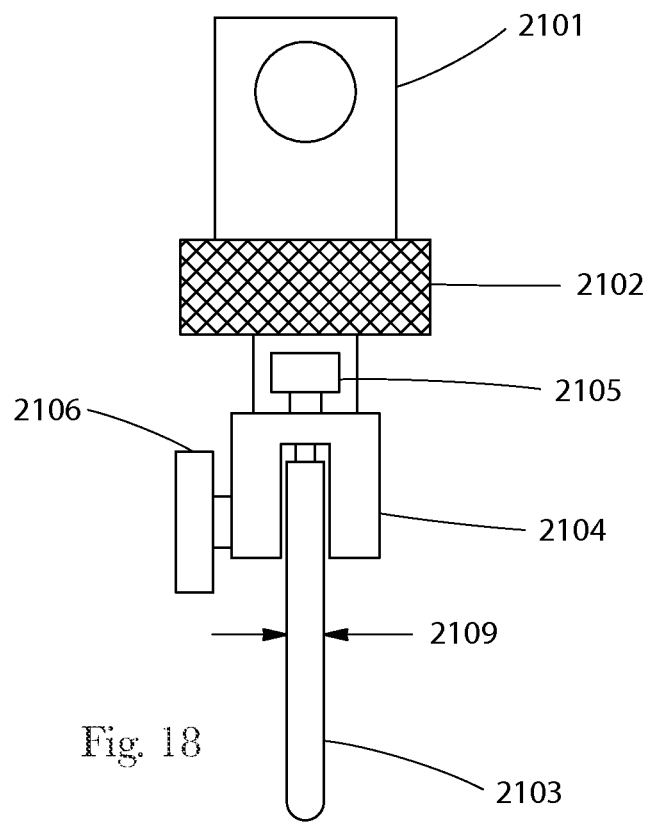
FIG. 18 is a side elevation view showing a plunger for use with the apparatus of FIG. 16.
Figure 19:
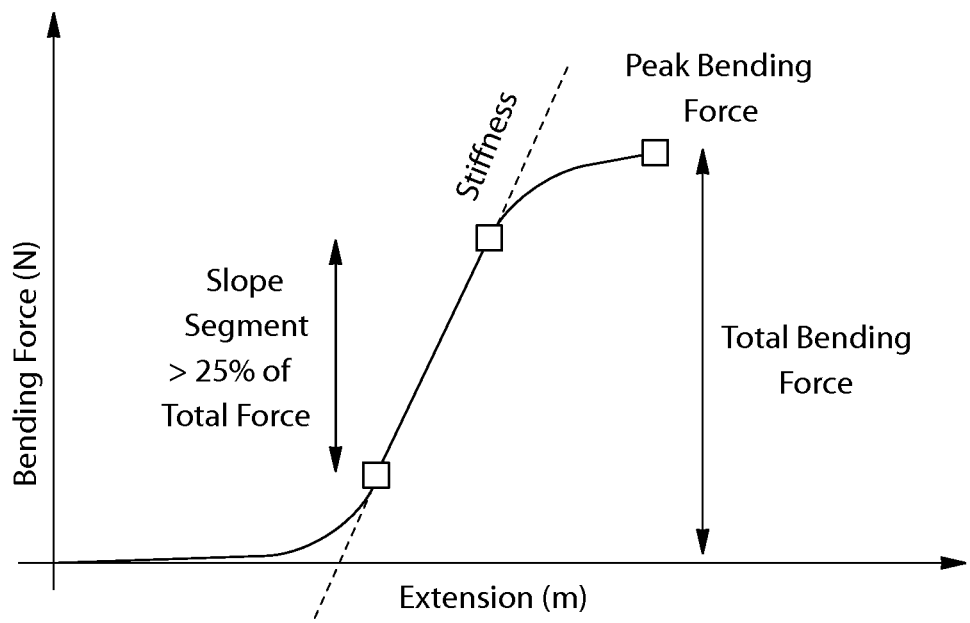
FIG. 19 is a graph showing Peak bending load and slope calculation areas on bending curve.

In one embodiment, at least one of, or even both the nonwoven layers 281 and 284 of an absorbent core extend from a portion of the front section 128, which is proximate the front edge of the absorbent article, to a portion of the back section 328 (inclusive of the middle section 228), which is proximate the back edge of the absorbent article. The absorbent material 283 may be present in the absorbent core along substantially the whole length of the nonwoven layers 281 and 284 as schematically represented in FIG. 11 with the absorbent material 283 represented with angled lines, it may be advantageous to include absorbent material 283 in the front and middle sections 128, 228 of the absorbent article but to limit the overall amount of absorbent material in the back section of the absorbent article such that the transverse axis Te of the ears and/or Tf of the fastening tabs go through a region of the absorbent core, which includes less absorbent material than the front and middle sections 128, 228. In one embodiment schematically represented in FIG. 12, the absorbent material 283 may be applied on the portion of the absorbent core present in the back section but at a lower basis weight than the absorbent material present in the middle section 228. In another embodiment schematically represented in FIG. 13, the absorbent material 283 may be disposed in only a portion of the back section 328 leaving the portion of the back section proximate the back edge of the absorbent article with only an insignificant amount of absorbent material. In yet another embodiment schematically represented in FIG. 14, the portion of the absorbent core 28 disposed in the back section 328 includes an insignificant amount of absorbent material or even no absorbent material. In one embodiment schematically represented in FIG. 15, at least one of, or even both the nonwoven layers 281 and 284 of an absorbent core extend from a portion of the front section 128, which is proximate the front edge of the absorbent article, to a portion of the back section 328 (inclusive of the middle section 228), which is proximate the line that separates the middle and back sections 328. An absorbent material 283 is disposed between the nonwoven layers 281, 284 leaving a substantially portion of the back section 328 with essentially no absorbent core. Among other benefits, it is believed that limiting the overall amount of absorbent material 283 in the back section 328 renders the back section 328 more flexible and allows the back section to better conform and remain in close contact with the skin of the wearer.

Peak Bending Force.

As previously discussed, it can be advantageous to provide an absorbent article having at least a back section that is flexible. This may be accomplished by significantly reducing the amount of cellulosic material present in the portion of the absorbent core present in the back section of the absorbent article. It is believed that a cellulosing material can stiffen regions of the article where it is present, in particular when a stack of folded absorbent articles are compressed to be packaged. Additional flexibility may further be obtained by significantly reducing the amount of absorbent material present in the portion of the absorbent core, which is present in the back section of the article. Further flexibility may also be obtained by reducing the amount of thermoplastic adhesive material present in the portion of the absorbent core, which is present in the back section of the article. In one embodiment, the Average Peak Bending Force of the rear region of back section 38 of an absorbent article is less than 0.08N, less than 0.07N, less than 0.06N or even less than 0.05N.

Bending Stiffness Measurement Method

Peak Bending Force and Bending Stiffness are measured using a constant rate of extension tensile tester with computer interface (a suitable instrument is an MTS Alliance under TestWorks 4 software, as available from MTS Systems Corp., Eden Prairie, Minn.) fitted with a 10 N load cell. A plunger blade 2100, shown in FIG. 9 (front view) and FIG. 10 (side view), is used for the upper movable test fixture. Base support platforms 2200, shown in FIG. 8, are used as the lower stationary test fixture. All testing is performed in a conditioned room maintained at about 23° C.±2 C and about 50%±2% relative humidity.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two horizontally movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 25.00±0.02 mm between the two gap edges of the support platforms 2204, with the plunger blade 2103 accurately (±0.02 mm) centered in the gap. Set the gauge length from the bottom of the plunger blade 2103 to the top surface of the support platform 2204 to 15 mm. Program the tensile tester to perform a compression test, collecting force and extension data at an acquisition rate of 400 Hz as the crosshead lowers at a rate of 500 mm/min for a total distance of 35 mm.

Precondition samples at about 23° C.±2° C. and about 50%±2% relative humidity for 2 hours prior to testing. The absorbent article is unfolded and placed with the wearer-facing surface facing upward. Using scissors cut the elastics along the longitudinal edges of the article at an interval of approximately 2 cm, such that the article can be laid flat. With a calibrated ruler, measure the longitudinal length of the article to the nearest 1 mm. Measure a distance equal to 20% of the article's longitudinal length, originating from the back waist edge of the article, along the longitudinal axis of the article, Mark the surface of the article at this intersection. With a hydraulic press and cutting die (63.5 mm square±0.1 mm and 25 mm deep), cut a specimen centered on this mark through all the layers of the absorbent article with the specimen's cut edges parallel and perpendicular to the longitudinal and lateral axis of the article.

Place the specimen flat onto the surface of the support platform 2204 over the gap 2209 with the wearer-facing surface facing upward. Center the specimen 1009 under the blade. The specimen is placed such that the direction corresponding to the lateral axis of the absorptive article it was harvested from is parallel to the length of the blade. Zero the load cell; start the tensile tester and the data acquisition.

Program the software to calculate the maximum Peak. Bending Force (N) and

Stiffness (N/m) from the constructed force (N) verses extension (m) curve. Stiffness is calculated as the slope of the bending force/extension curve for the linear region of the curve (see FIG. 11), using a minimum line segment of at least 25% of the total peak bending force to calculate the slope.

Report Peak Bending Force to the nearest 0.01 N and the Bending Stiffness to the nearest 0.1 N/m, and record the results. Repeat the test and record the results for 10 samples. Calculate the average Peak Bending Force and average Bending Stiffness.

Examples

| Product name | Average Peak Bending Force at Waist (N) | Standard Deviation |
|---|---|---|
| Example A | 0.06 | 0.02 |
| Pampers Cruisers (Size 4) | 0.14 | 0.03 |
| Pampers Easy Ups (Size 5) | 0.82 | 0.1 |
| Pampers Baby Dry (Size 5) | 0.12 | 0.03 |
| Luvs (Size 4) | 0.10 | 0.02 |
| Luvs (Size 2) | 0.08 | 0.01 |
| Huggies Little Movers (Size 5) | 0.64 | 0.06 |
| Huggies Snug & Dry (Size 5) | 0.96 | 0.28 |
| Huggies Pull Ups (Size 3T/3T) | 0.82 | 0.21 |
| Target Brand (Size 5) | 0.3 | 0.03 |

Pampers and Luvs products are manufactured by The Procter & Gamble Company
Huggies products are manufactured by Kimberly-Clark
Example A is representative of one embodiment of the invention and include an absorbent core described in the context of FIG. 10.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It should be apparent that combinations of such embodiments and features are possible and can result in executions within the scope of this invention. It is therefore intended to cover in the appended claims all such changes and modifications that are within the scope of this invention.

What is claimed is:

1. A disposable absorbent article comprising:
   a) a chassis having a front region with a front edge, a rear region with a back edge, a crotch region between the front region and the rear region, and a pair of opposing longitudinal edges, said chassis comprising an absorbent core having front and back edges;
   b) first and second elastically elongatable ears, each of said first and second elastically elongatable ears having upper and lower edges and a transverse axis, each of said upper and lower edges of said elastically elongatable ears having proximal and distal ends, said first and second ears defining a back section of said absorbent article that is present between said back edge of said chassis and a line connecting the respective proximal ends of the lower edges of said first and second elastically elongatable ears, wherein the upper and lower edges of said first and second elongatable ears are asymmetric relative to the transverse axis of the elastically elongatable ears; and
   c) first and second fastening tabs respectively connected said first and second elastically elongatable ears, each of said first and second fastening tabs having upper and lower edges and a transverse axis, each of said upper and lower edges of said fastening tabs having a proximal end, wherein the upper and lower edges of said fastening tabs are asymmetric relative to the transverse axis of the fastening tabs, wherein the transverse axis of the first and second fastening tabs overlap substantially with the transverse axis of the first and second elongatable ears respectively, wherein a first portion of said back section of said absorbent article that is positioned between said back edge of said chassis and said back edge of said absorbent core has an average caliper of less than 0.75 mm, wherein a second portion of said back section of said absorbent article includes a portion of said absorbent core and has an average caliper of less than 0.75 mm;

wherein the back section of the absorbent article has an Average Caliper Differential of between 0.1 mm and 0.25 mm;

wherein said first and second elastically elongatable ears are connected to said chassis such that the transverse axis of each of said first and second fastening tab is disposed between said back edge of the chassis and said back edge of said absorbent core; and wherein said transverse axis of the elastically elongatable ears is separated from the back edge of the absorbent core by a distance of less than 50 mm.

2. The disposable absorbent article of claim 1 wherein said absorbent core contains less than 10% by weight of the absorbent core of cellulosic fibers.

3. The disposable absorbent article of claim 1 wherein the back edge of the chassis and the back edge of the absorbent core are separated by a longitudinal distance of less than 100 mm.

4. The disposable absorbent article of claim 1 wherein said absorbent core is substantially cellulose free.

5. The disposable absorbent article of claim 4 wherein said absorbent core contains less than about 5% by weight of the absorbent core of cellulosic fibers.

6. The disposable absorbent article of claim 4 wherein said absorbent core comprises a first layer of a nonwoven fibrous material having upper and lower surfaces, a layer of a thermoplastic adhesive material and an absorbent material between the upper surface of the first layer of the nonwoven fibrous material and the layer of thermoplastic adhesive material.

7. The disposable absorbent article of claim 6 wherein the upper surface of the first layer of nonwoven material comprises a plurality of regions that are each in direct facial relationship with a significant amount of said absorbent material.

8. The disposable absorbent article of claim 7 wherein said upper surface of said first layer of nonwoven fibrous material comprises a plurality of regions that are each in facial relationship with an insignificant amount of said absorbent material.

9. The disposable absorbent article of claim 8 wherein said absorbent core further comprises a second layer of a nonwoven fibrous material having upper and lower surfaces such that said absorbent material and said layer of thermoplastic adhesive material are between said upper surface of said first layer of nonwoven fibrous material and said second layer of said nonwoven fibrous material.

10. The disposable absorbent article of claim 9 wherein the lower surface of the second layer of nonwoven material comprises a plurality of regions that are each in direct facial relationship with a significant amount of additional absorbent material.

11. The disposable absorbent article of claim 10 wherein said lower surface of said second layer of nonwoven fibrous material comprises a plurality of region that are each in facial relationship with an insignificant amount of said additional absorbent material.

12. The disposable absorbent article of claim 11 wherein at least some of the regions of said upper surface of the first nonwoven fibrous material that are in direct facial relationship with an absorbent material are in direct facial relationship with at least corresponding regions of the lower surface of the second nonwoven fibrous material that are in facial relationship with an insignificant amount of absorbent material.

13. The disposable absorbent article of claim 9 wherein said first layer of nonwoven fibrous material and said second layer of nonwoven fibrous material are made of different nonwoven materials.

14. The disposable absorbent article of claim 9 wherein said first layer of nonwoven fibrous material and said second layer of nonwoven fibrous material each have a surface energy and wherein the surface energy of said first layer is different from the surface energy of said second layer.

15. The disposable absorbent article of claim 14 wherein said second layer of nonwoven fibrous material comprises a surfactant.

16. The disposable absorbent article of claim 15 wherein said article comprises a middle section having an average caliper that is greater than the average caliper of said back section.

* * * * *